US006376697B1

(12) United States Patent
Aneja

(10) Patent No.: US 6,376,697 B1
(45) Date of Patent: Apr. 23, 2002

(54) LABELLED PHOSPHOINOSITIDES AND ANALOGUES

(75) Inventor: Rajindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 0 days.

(21) Appl. No.: 09/292,242

(22) Filed: Apr. 15, 1999

Related U.S. Application Data

(60) Provisional application No. 60/081,847, filed on Apr. 15, 1998.

(51) Int. Cl.$^7$ .......................... C07F 9/117; C07F 9/177

(52) U.S. Cl. .................. 558/160; 424/1.77; 558/161; 558/177; 558/180; 558/183; 558/186

(58) Field of Search .................. 424/1.77; 558/160, 558/161, 177, 180, 183, 186

(56) References Cited

U.S. PATENT DOCUMENTS 5,227,508 A    7/1993   Kozikowski et al. ........ 558/155

OTHER PUBLICATIONS

Aneja et al., "A General Synthesis of Glycerophospholipids," *Biochim Biophys. Acta*, 218:102–111, 1970.
Aneja and Parra., "Facile Optical Resolution of DL–1,4,5, 6–Tetra–O–Benzyl–MYO–Inositol: Key Synthons for the Phosphoinositides," *Tetrahedon Lett.*, 35:525–526, 1994.
Aneja et al., "The Absolute Configuration and Optical Purity of (–)– and (+)–1,2:4,5–Di–O–Cyclohexylidene–Myo–Insitols," *Tetradhedron Asymmetry*, 6:17–18, 1995.
Aneja et al., "A Unified Approach to Umambiguous Synthesis of the Phosphatidylinositol–3–Phosphates Involved in Intracellular Signal Transduction," *Tetrahedron Lett.*, 38:803–806, 1997.
Bannwarth and Trzeciak, "A Simple and Effective Chemical Phosphorylation Procedure for Biomolecules," *Helv. Chim. Acta*, 70:175–186, 1987.
Berridge, "Inositol Trisphosphate and Diacylglycerol: Two Interacting Second Messengers," *Annu. Rev. Biochem.*, 56:159–163, 1987.
Berridge, "Inositol Trisphosphate and Calcium Signalling," *Nature*, 361:315–325, 1993.
Bruzik and Kubiak, "General Synthesis of Phosphatidylinositol 3–Phosphates," *Tetrahedron Lett.*, 36:2415–2418, 1995.
Chen et al., Synthesis of Photoactivatable 1,2–O–Ddiacyl–sn–Glycerol Derivatives of 1–L–Phosphatidyl–D–MYO–Inositol 4,5–Bisphosphate (PtdInsP$_2$) and 3,4,5–Trisphosphate(PtdInslP$_3$), *J. Org. Chem.*, 61:6305–6312, 1996.
Chen and Prestwich, "Synthesis of a Tritium–Labelled Diether Analog of Phosphatidylinositol 4,5–Bisphosphate," *J. Labelled Compounds and Radiopharmaceuticals*, 39:251–258, 1997.

Duckworth and Cantley, "PI 3–Kinase and Receptor–Linked Signal Transduction," *Lipid Second Messengers—Handbook of Lipid Research*; Plenum Press: New York, NY, vol. 8, pp 125–175, 1996.
Gaffney and Reese, "Synthesis of 1–O–Stearoyl–2–O–Arachidonoyl–sn–Glycer–3–YL–D–MYO–Inositol 3,4,5–Trisphosphate and its Stereoisomers," *Bioorg. Med. Chem. Lett.*, 7:171–3176, 1997.
Gou and Chen, "Synthesis of L$\mu$ Phosphatidyl–D–MYO–Inositol 3,4,5–Trisphosphate, an Important Intracellular Signalling Molecule," *J. Chem. Soc., Chem. Commun.*, 2126–2126, 1994.
Grove et al., "Synthesis of Dipalmitoyl Phosphatidylinositol 3,4–bis(phosphate) and 3,4,5–tris(phosphate) and their Enantiomers," *J. Chem. Soc., Chem. Commun.*, 1635–1636, 1997.
Lee and Rhee, "Significant of PIP$_2$ Hydrolysis and Regulation of Phospholipase C Isozymes," *Curr. Opin. Cell Biol.*, 7:183–189, 1995.
Stephens et al., "Synthesis of Phosphatidylinositol 3,4, 5–Trisphosphate in Permeabilized Neutrophils Regulated by Receptors and G–Proteins," *J. Biol. Chem.*, 268:17162–17172, 1993.
Terui et al., "Effects of Acid Phospholipids on Nucleotide Exchange Properties of ADP–Ribosylation Factor 1," *J. Biol. Chem.*, 269:28130–28135, 1994.
Toker et al., "Activation of Proetin Kinase C Family Members by the Novel Polyphosphoinositides PtdIns–3,4,p$_2$ and PtdIns–3,4,5–P$_3$," *J. Biol. Chem.*, 269:32358–32367, 1994.
Watanabe et al., "Synthesis of a Phosphatidylinositol 3,4, 5–Trisophosphate," *Tetrahedron Lett.*, 35:123–124, 1994.
Watanabe et al., Synthesis of 1D–Distearoylphosphatidyl–MYO–Insitol 3,4,5–Tris(dihydrogen Phosphate), *Tetrahedron*, 51:8969–8976, 1995.
Watanabe et al., "Protection of Phosphate with the 9–fluorenylmethyl Group. Synthesis of Unsaturated–Acyl Phosphatidylinositol 4,5–Bisphosphate," *Tetrahedron Lett.*, 38:7407–7410, 1997.
Watanabe and Nakatomi, "Synthesis of Natural PI(3,4, 5)P$_3$," *Tetrahedron Lett.*, 39:1583–1586, 1998.

(List continued on next page.)

*Primary Examiner*—Michael G. Ambrose
(74) *Attorney, Agent, or Firm*—Williams, Morgan and Amerson

(57) ABSTRACT

The present invention provides novel compounds comprising cellular phosphoinositides and analogues tagged with stable or radioactive isotopes. The present invention also provides novel methods for the preparation of the said phosphoinositides by syntheses, and novel key intermediates of synthesis; the novel methods of synthesis are applied also for the preparation of the phosphoinositides in non-labelled form. In addition, the present invention discloses a class of novel compounds as isotope labelled key precursors of labelled phosphoinositides. These precursors are derivatives of the target phosphoinositides, labelled with stable or radioactive isotopes, wherein OH and phosphate groups are blocked with temporary protecting groups.

29 Claims, No Drawings

OTHER PUBLICATIONS

Whitman et al., "Evidence for Two Distinct Phosphatidylinositol Kinases in Fibroblasts," *Biochem. J.*, 247:165–174, 1987.

Whitman et al., "Type I Phosphatidylinositol Kinase makes a Novel Inositol Phospholipid, Phosphatidylinositol–3–Phosphate," *Nature*, 332:644–646, 1988.

STN International, CAPLUS Database, Chemical Abstracts Service, (Columbus, Ohio), Accession No. 1995:692419; Cottaz, S. et al., J. Chem. Soc. Perkin Trans. 1 (13), 1673–1678 (1995), abstract.

STN International, CAPLUS Database, Chemical Abstracts Service, (Columbus, Ohio), Accession No. 1995:421206; Khoom, K–H et la., Glycobiology 5(1), 117–127 (1995), abstract.

STN International, CAOLD Database, Chemical Abstracts Service, (Columbus, Ohio), Accesion No. CA55:25769d; Stanacev, N.Z. et al. J. Org. Chem. 26, 912–918 (1961).

LABELLED PHOSPHOINOSITIDES AND ANALOGUES

The present application claims priority to co-pending U.S. provisional application Serial No. 60/081,847, filed Apr. 15, 1998. The entire text and figures of this disclosure is specifically incorporated herein by reference without disclaimer.

The present invention was partially made with funds provided by the Department of Health and Human Services under Grants No. NIH GM58992 and GM49594. Accordingly, the United States Government owns certain rights in this invention.

BACKGROUND OF THE INVENTION 10 1. Field of the Invention

The present invention provides novel compounds phosphoinositides and analogues tagged with stable or radioactive isotopes, novel methods for their preparation by syntheses, and novel key intermediates of synthesis; the novel methods of synthesis are applied also for the preparation of the phosphoinositides in non-labelled form.

2. Related Art

Several phosphoinositides of eukaryotic cells, including 1D-1-(1'-O-fattyacyl'-2'-O-fattyacyl -sn-glycero-3'-phospho)-myo-inositol (phosphatidylinositol, PtdIns), phosphatidylinositol-4-phosphate (PtdIns-4-P), and phosphatidylinositol-4,5-bisphosphate (PtdIns-4,5-$P_2$) have been well known as metabolically vital lipid precursors of the intracellular second messengers 1D-myo-inositol-1,4,5-trisphosphate and 1,'2'-diacyl-sn-glycerol (see Berridge, M. J. 1987, Annu. Rev. Biochem., 56: 59). Recently, the D-3-phosphorylated phosphoinositides, including the phosphatidylinositol 3-phosphate (PtdIns-3-P), phosphatidylinositol 3,4-bisphosphate (PtdIns-3,4-$P_2$), phosphatidylinositol 3,5-bisphosphate (PtdIns-3,5-$P_2$), phosphatidylinositol 3,4,5-trisphosphate (PtdIns-3,4,5-$P_3$) have been encountered in eukaryotic cells (Whitman, M., et al., 1987, Biochem. J., 247: 165; Whitman, M., et al., 1988, Nature, 332: 644 ), and, recognized as intracellular messengers (Stephens, L., et al., 1993, J. Biol. Chem., 268: 17162; Duckworth, B. C. and Cantley, L. C. Lipid Second Messengers—Handbook of Lipid Research; Plenum Press: New York, N.Y. 1996, Vol 8, pp 125–175.). Thus the phosphoinositides, and their metabolites, regulate vital biological signaling, and as such, are important materials for research studies, diagnostics reagents, and biotechnology aids. The various enzyme systems involved in the signal transduction via the phosphoinositides, especially the phosphoinositide-specific lipases A, C and D, the phosphoinositide kinases, and phosphoinositide-phosphate phosphatases regulate vital metabolic and physiological processes including cell division, growth and apoptosis. Therefore, phosphoinositides and analogues are being studied for the development of new drug modalities for aberrant signaling including some types of cancer (Kozikowski, A. P. et al., 1993, U.S. Pat. No. 5,227,508).

The phosphoinositides are extremely minor components of plasma and nuclear membranes of cells. Small quantities of PtdIns, PtdIns-4-P, and PtdIns-4,5-$P_2$ can be obtained from natural sources, such as bovine brains, but the D-3-phosphorylated types are not available. The isolated materials are mixtures of molecular species differing in the nature and proportion of the integral fattyacyl ester residues. Individual molecular species with specified fattyacyls or equivalent are required as biochemical research reagents and must be prepared by synthesis. The utility of biochemical research reagent is enhanced by tagging the molecule with isotope labels, including radioactive atom labels, and phosphoinositides with such labels are useful materials.

In the prior art, labelled phosphoinositides have been prepared from tritium labelled myo-inositol using the biochemical machinery of intact cells; alternatively, the biochemical reaction of $^{32}P$ labelled ATP catalyzed by PtdIns kinase enzymes has been used to introduce an additional phosphate albeit with $^{32}P$ into bovine brain derived phosphoinositides (see Stephens, L., et al., 1993, J. Biol. Chem., 268: 17162; Duckworth, B. C. and Cantley, L. C. Lipid Second Messengers—Handbook of Lipid Research; Plenum Press: New York, N.Y. 1996, Vol 8, pp 125–175). The routes are ineffcent, limited to minute quantities, and in case of kinase enzymes are practical only in the very few laboratories with access to these enzymes. All labelled phosphoinositides so produced are mixtures of molecular species differing in the nature and proportions of the integral fattyacyl ester residues; individual molecular species must be prepared by synthesis, and appropriate synthetic methods are not available.

Only one chemical route has been described whereby a diether analogue of PtdIns-4,5-$P_2$ labelled with tritium was obtained; herein, the tritium label was introduced in the alkyl-ether chain by metal catalyzed reduction of a C—C double bond with tritium gas (Chen, J. and Prestwich, G. D., 1996, J. Labelled Compounds and Radiopharmaceuticals, 39: 251–258). The method is not applicable to phosphoinositides with (poly)unsaturated fattyacyls, and for labeling at other locations, particularly in the inositol and glycerol residues; overall the method is inadequate.

Several chemical syntheses of the phosphoinositides without isotope labels have been described (for example, Aneja, S. G., et al., 1997, Tetrahedron Lett., 38: 803; Bruzik, K. S. and Kubiak, R. J. 1995, Tetrahedron Lett., 36: 2415; Chen, J., et al., 1996, J. Org. Chem., 91: 6305; Desai, T., et al., 1996, Special Publication—Royal Society of Chemistry, 180: 67; Gaffney, P. R. J. and Reese, C. B., 1997, Bioorg. Med. Chem. Lett., 7: 3171; Gou, D.-M. and Chen, C.-S., 1994, J. Chem. Soc., Chem. Commun., 2125; Grove, S. J. A., et al., 1997, J. Chem. Soc., Chem. Commun., 1635; Toker, A., et al., 1994, J. Biol. Chem., 269: 32358; Watanabe, Y., et al., 1994, Tetrahedron Lett., 35: 123; Watanabe, Y., et al., 1995, Tetrahedron, 51:8969; Watanabe, Y. and Nakatomi, M., 1998, Tetrahedron Lett., 39: 1583). Most of these syntheses are applicable only to analogues with saturated fattyacyls at sn-glycero-1',2'-O locations. The two most recent (Gaffney and Reese, 1997; Watanabe and Nakatomi, 1998) address the synthesis of phosphoinositides with unsaturated fattyacyls. As mentioned, these methods are not suitable for labelling phosphoinositides, and have not been so applied.

SUMMARY OF THE INVENTION

The present invention pertains to phosphoinositides and novel analogues tagged with stable or radioactive isotopes, novel methods for their preparation by syntheses, and novel key intermediates of synthesis. The analogues include but are not limited to structural and stereochemical isomers of the cellular phosphoinositides, the corresponding thiophosphates and phosphonates, and the radyl and sphingo type inositolphospholipids. The novel labelled compounds are closely related to the cellular phosphoinositides shown in the generalized structure below.

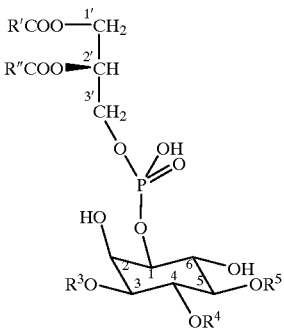

Phosphoinositides
R'CO, R"CO = Fattyacyls
$R^3, R^4, R^5$ = H or $P(O)(OH)_2$

The labels are provided preferably as deuterium and tritium isotopes of hydrogen, and radioactive isotopes of phosphorus and sulphur, but are not limited to these atoms. Labels are located at selected positions in the lipid or the inositol(phosphate) residues of phosphoinositide structure and are variously in the fattyacyl or alkyl chain(s), the glycero residue, the inositol residue, phosphate, thiophosphate, phosphonate or equivalent group(s). Labels are introduced at selected positions by way of novel synthons which carry temporary protecting groups at positions other than the label site, and this site consequently is amenable to selective labeling. The design and synthesis of these temporarily protected synthons is an critical element of the present invention. The novel methods of preparation are multi-step syntheses and comprise assembly of the complete phosphoinositide skeleton from phosphatidyl and inositol (phosphate) synthons. The isotope atoms are introduced at relatively late stage during synthesis of these aforementioned synthon types and assembly of the phosphoinositide skeleton from the synthons. The late stage option is desirable, particularly for radioactive isotope labels because it minimizes handling of radioactive materials and waste disposal, and thus is beneficial for personnel and environmental safety. Although the emphasis is on labelled materials and methods for the preparation thereof, the novel methods of synthesis are shown to be suitable and valid for phosphoinositides with the normal stable isotope compositions based on $^1H$, $^{31}P$, and $^{32}S$ atoms. The chemistry and protocols for products with or without isotope labels are identical and hence synthesis of either type is sufficient validation of the novel methodology. Individual molecular species of the phosphoinositides, with or without isotope labels, and their analogues and metabolites are useful as research biochemicals, diagnostic reagents, biotechnology process aids, and models for the development of drugs for treatment of aberrant signaling.

The isotope atom label may be located in the fattyacyl, glycerol, inositol and phosphate residues of the phosphoinositide structure, at specified single positions, or at multiple sites; all provide useful reagents. The labelled phosphoinositides can be monitored in the intact state or after biological interactions and transformations. These transformations can result in enzyme catalyzed fragmentation or addition of more groups such as phosphates. Several enzyme and effector protein systems have been characterized which interact with the phosphoinositides in the signaling cascades and metabolic pathways. The phosphoinositide PtdIns-4,5-$P_2$ functions as the preferred substrate of the PI-PLC (Lee, S. B. and Rhee, S. G. 1995, Curr. Opin. Cell Biol., 183) and the phosphoinositide 3-kinase (PtdIns 3-kinase) enzyme families (Duckworth, B. C. and Cantley, L. C., 1996, loc cit.), and, as allosteric activating factor of cellular regulatory proteins with and without pleckstrin homology (PH) domains (Terui, T., et al, 1994, J. Biol. Chem., 269: 28130).

The action of PI-PLC on PtdIns-4,5-$P_2$ causes hydrolysis to the two intracellular second messengers 1D-myo-inositol-1,4,5-trisphosphate and 1',2'-diacyl-sn-glycerol (Berridge, M. J., 1993, Nature, 361: 315). Phospholipase $A_2$ specifically releases the fattyacyl from the sn-glycero-2'- position with concomitant formation of the corresponding lyso-phosphoinositide. PtdIns kinases (e.g., PtdIns 3-kinase) introduce phosphate groups into phosphoinositides and the PtdIns-phosphate phosphatases (e.g., PTEN), remove phosphate groups from inositol positions specific to each enzyme. Tritium labelled phosphoinositides are generally useful for monitoring such transformations, and deuterium labelled analogues are useful for defining metabolites in vivo in human subjects by analyses using (HPLC coupled to) mass spectrometry.

Several phosphoinositides with 1',2'-dipalmitoyl-sn-glycero lipid residue have become available recently. These synthetic analogues have contributed significantly to the current state of knowledge about the functions of the phosphoinositides as signal mediators, and have become established as important biochemical reagents. Labelled analogues of these, the 1'-saturated fattyacyl-2'-unsaturated fattyacyl-sn-glycero lipid residue types akin to the cellular phosphoinositides, and, analogues including structural and stereochemical isomers are required as research and diagnostic reagents. The present invention is concerned with all these materials, methods for their preparation by synthesis, and important intermediates in the synthetic methods.

As mentioned, the prior art methods are not suitable for preparing individual molecular species of labelled phosphoinositides, and have not been so applied. The novel methods of synthesis of the present invention are designed specifically for labelled phosphoinositides, and additionally provide concise syntheses of the non-labelled species; the latter are useful research reagents in their own right.

BRIEF DESCRIPTION OF THE SCHEMES

Scheme 1: Illustrates labelling of preformed phosphoinositide derivative with hydrogen isotopes.

Scheme 2: Is a reaction scheme for synthesis of labelled DPPtdIns-3,4,5-$P_3$.

Scheme 3: Illustrates the synthesis of DPPtdIns-3,4,5-$P_3$.

Scheme 4: Shows synthesis of SAraPtdIns-3,4,5-$P_3$.

Scheme 5: Synthesis of 1D-6-O-trichloroacetyl-myo-inositol-3,4,5-tris(trichloroethylphosphate).

Scheme 6: Preparation of 1-O-stearoyl-2-O-arachidonyl-sn-glycero-3-phosphoric acid.

Scheme 7: Preparation of Phosphatidyl-inosose esters.

DETAILED DESCRIPTION OF THE INVENTION

The present invention provides novel compounds comprising phosphoinositides and analogues tagged with stable or radioactive isotopes depicted by the structure 1. The present invention also provides novel methods for their syntheses, novel key starting materials, novel key intermediates including labelled chemical precursors for the preparation of the said labelled phosphoinositides. The novel methods of synthesis are applied also for the preparation of the phosphoinositides in non-labelled form. Individual molecular species of the phosphoinositide compounds with specified fattyacyls or equivalent lipid are obtained; these phosphoinositide compounds are useful as biochemical reagents in research and diagnostics, biotechnological process aids, and for the development of novel therapeutic drug modalities based on signal transduction via the phosphoinositides.

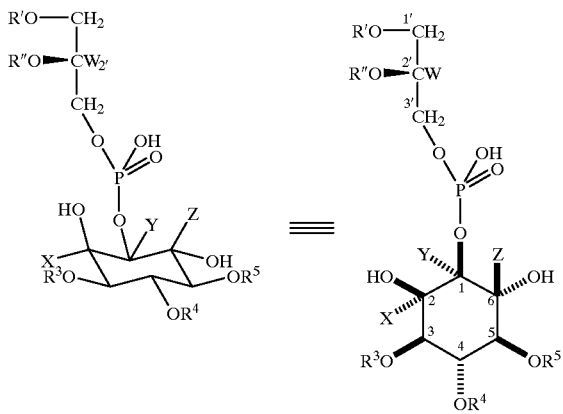

1: W, X, Y, Z = $^3$H, $^2$H, or $^1$H, wherein at least one of W, X, Y or Z is $^3$H, $^2$H;
R', R" = Fattyacyl, Alkyl or H;   $R^3$, $R^4$, $R^5$ = H, P(O)(OH)$_2$ The absolute stereochemistry shown in 1 is that of naturally occurring phosphoinositides wherein the 1',2'-diacyl-sn-glycero-3'-phospho moiety (commonly referred to as the phosphatidyl residue) is esterified with 1-OH of the 1D-1-(-myo-inositol) enantio residue; the present invention encompasses this natural stereochemistry as well as structural and stereochemical isomers.

The predominant molecular types in the cellular phosphoinositides are considered to be basedonthe1D-1-(1'-O-stearoyl-2'-O-arachidonyl-sn-glycero-3'-phospho)-myo-inositol-structural motif (1: R'=stearoyl; R"=arachidonyl) varying in the number and location(s) of phosphate groups. The present invention provides methods for synthesis of all 1-saturated fattyacyl-2-unsaturated fattyacyl species. The methods also provide analogues with two identical saturated fattyacyls (e.g. R'=R'=palmitoyl), or acyl-alkyl (R', R"=acyl or alkyl), the radyl type 1',2'-dialkylether (R', R"=alkyl), and their partially or fully deacylated metabolites (R'=acyl or alkyl, R"=H). Further, these methods provide sphingophosphoinositol analogues of the phosphoinositides wherein the glycerolipid residue in structure 1 is replaced by ceramide or sphingosine derivatives; other analogues are the corresponding thiophosphates ($R^3$, $R^4$ or $R^5$=P(S)(OH)$_2$) and phosphonates (a C—P bond in place of O—P in the link to glycerol or inositol). The stereochemical isomers are formed from sn-glycero-1'-phospho or rac-glycero, and 1L-1(-myo-inositol) or DL-1(myo-inositol) moieties.

Labels are located at selected positions in the inositol (phosphate) or the lipid fattyacyl/ alkyl chain(s), glycero or sphingo residues of phosphoinositide analogue structures. Preferably labels are provided as the $^2$H or $^3$H isotopes of hydrogen at selected positions, particularly at positions 1, 2 or 6 of the inositol residue (X,Y, Z=$^1$H, $^2$H, or $^3$H); other label sites are in glycero residue, for instance at the sn-glycero-2'- position, and at selected positions along the fattyacyl chains R' or R". Those of ordinary skill in the art would appreciate the chemical structures for such labelled compounds based upon the text, structures and reaction schemes of the present disclosure.

The present invention provides single molecular species of labelled phosphoinositide compounds. A "labelled phosphoinositide compound", as used succinctly herein, means a phosphoinositide compound that comprises at least a first stable or radioactive isotope. The "at least a first stable or radioactive isotope" is at least a first "type" of stable or radioactive isotope, which label or isotope may be incorporated into the phosphoinositide compound at one or more positions. Labels such as $^2$H, $^3$H, $^{13}$C, $^{14}$C, $^{32}$P, $^{33}$P or $^{35}$S isotopes exemplify the invention, with $^2$H and $^3$H being preferred in certain contexts.

Although various individual labelled compounds are provided, each may be obtained free from other species, rather than as a mixture. Essentially pure formulations of labelled phosphoinositide compounds are therefore provided. This in no way excludes the later combination, or admixture, of any originally pure, labelled phosphoinositide compound with any other labelled or unlabelled phosphoinositide compound, or indeed, with any other compound, or cellular component.

The present invention provides compositions comprising essentially, or substantially, a single molecular species of a labelled phosphoinositide. This means that the fattyacyls at the 1-10 glycero position are identical in all molecules, and that fattyacyls at the 2-glycero position are also identical in all molecules, although the fattyacyls at 1- and 2- positions may be non-identical. These compositions comprise one species of labelled phosphoinositide, isolated free from other species of labelled or unlabelled phosphoinositide. The invention further provides labelled phosphoinositides essentially separated free from all other molecular species, including precursors, synthons and contaminants. Therefore, the present invention provides compositions comprising substantially pure labelled phosphoinositides, i.e., substantially pure phosphoinositide compounds that comprise at least a first stable or radioactive isotope incorporated at least at a first position within the compound.

In certain preferred embodiments, this invention provides labelled phosphoinositide compounds, essentially pure labelled phosphoinositide compounds, and compositions comprising substantially purified labelled phosphoinositide compounds that comprise a (poly)unsaturated fattyacyl residue. A range of fatty acid residues may nonetheless by used in the invention.

In certain other preferred embodiments, the invention provides labelled phosphoinositide compounds, essentially pure labelled phosphoinositide compounds, and compositions comprising substantially pure labelled phosphoinositide compounds, wherein the label is comprised within the inositol or glycerol residue or component. However, labels incorporated within the fattyacyl and phosphate residues are also encompassed within the surprisingly effective methods of the invention.

Compositions comprising synthetic intermediates, precursors or "synthons" for use in generating isotopically labelled phosphoinositide compounds are also provided by the present invention. Where isotopic hydrogen labels are concerned, in particular, such synthetic intermediates generally comprise temporary protecting groups, i.e., hydroxyl protecting groups and phosphate protecting groups, at the hydroxyl and phosphate positions other than the position(s) into which the isotopic label is to be introduced.

In preferred methods for preparing isotopically labelled phosphoinositide compounds, and synthetic intermediates thereof, at least a first stable or radioactive isotope is introduced into the phosphoinositide compound, or synthetic intermediate, at a stage late in the synthesis. Accordingly, synthetic methods include:
(i) introducing at least a first stable or radioactive isotope into a fully assembled phosphatidylinositol skeleton; and
(ii) introducing at least a first stable or radioactive isotope into an inositol derivative and conjugating the labelled inositol derivative to a phosphatidyl residue.

Taking hydrogen isotope labels as an example, in the first general method, a fully assembled phosphatidylinositol skeleton is provided in a substantially protected form. A "substantially protected" form is a form in which all OH groups that are not intended to be labelled are protected, and yet in which there is at least one unprotected OH group into which the label can subsequently be introduced. The $^2$H or $^3$H isotope is then introduced via the unprotected OH group.

"Substantially protected" phosphoinositide compounds may also be termed "uniquely deprotected" phosphoinositide compounds. The meaning being the same, in that only the intended labelled target is available for reaction. The groups that are intended to remain unlabelled are protected, preferably by attachment to temporary, i.e., "removable", protecting groups.

The substantially protected phosphoinositide compound can then be reacted to introduce the isotope into the unprotected group. A preferred method uses an oxidation-reduction system, wherein an intermediate ketone group is formed, which can then be labelled with $^2$H or $^3$H. The protected groups are immune to this round of reactions.

The second approach also utilizes the same general selective protection and deprotection methodology, but the "substantially or selectively protected" starting compounds are myo-inositol compounds. These compounds have an unprotected OH group, such as an unprotected equatorial 1-OH group, and a plurality of protected OH groups, preferably attached to temporary protecting groups. $^2$H or $^3$H isotopes are introduced into the unprotected OH group, preferably by oxidation and reduction of an intermediate ketone group. The labelled inositol derivative is then coupled to a phosphatidyl residue.

Using either variation, to create an isotopically labelled phosphoinositide compound, rather than an intermediate thereof, the temporary protecting groups are removed from the OH groups that are not intended to be labelled.

The labelled phosphoinositides or labelled intermediates may carry single or multiple isotopic atom labels. Thus multiple labeling is achieved by incorporating the same isotope at two or more locations, preferably in different structural residues exemplified by fattyacyl, glycerol and myo-inositol. Multiple labeling is achieved also by incorporating different isotopic atoms into a molecule, as for example tritium and $^{32}$P respectively in glycerol and phosphate. Alternatively, these non-identical isotopes may be in the same part of the molecule. Thus a tritium as well as a phosphate may attached to the myo-inositol residue.

Labels are introduced by way of novel synthons and intermediates which carry temporary protecting groups at positions other than the label site which is left unprotected, and is thus amenable to chemical reaction for selective labeling. The molecular design of these temporarily protected synthons and intermediates is an important feature of the present invention.

Specifically, the present invention discloses a class of novel compounds as isotope labelled key precursors of labelled phosphoinositides. These precursors are derivatives of the target phosphoinositides, preferably labelled with hydrogen isotopes, wherein OH and phosphate groups are blocked with temporary protecting groups. Accordingly, by removing temporary protecting groups from OH and phosphate residues, these precursors are readily transformed into the target phosphoinositides labelled with hydrogen isotopes. The precursors corresponding to structure 1 with labels at positions 2-, 1- and 6- are shown in structures 2, 3 and 4. The protecting groups are selected inter alia to ensure that deprotection can be achieved without effecting other functional groups, such as unsaturation in the fattyacyl residues, discussed later in this Specification.

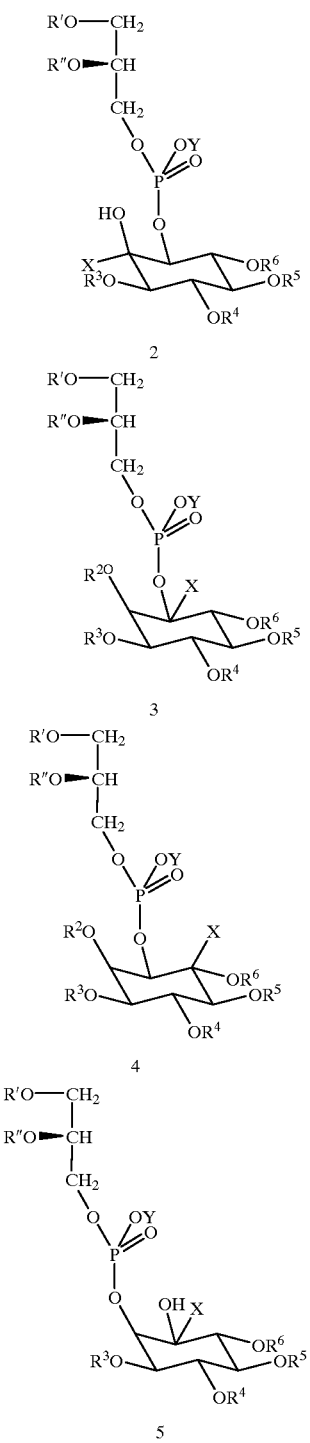

X = $^2$H or $^3$H; Y = Alkyl, CH$_3$ or OH;
R', R'' = Fattacyl, Alkyl or H; R$^2$ = H or OH protecting group;
R$^3$, R$^4$, R$^5$ = (OH protecting group) or (P(O)(O protecting group)$_2$)
or (P(O)(OH)(O protecting group)) or (P(O)(OH)$_2$)
R$^2$, R$^6$ = H or (OH protecting group)

Structure 5 illustrates a variation within the above group of precursors. 2-Phosphatidyl structures are obtained as by-product in the synthesis of the 1-phosphatidyl compounds prior to labeling, and the two are inter-converted by phosphatidyl migration. Thus, the 2-phosphatidyl isomer 5 is converted into 1-phosphatidyl series with a label incorporated at the 1-position.

Two complementary approaches for synthesis of the precursors 2–5 and hence of the target phosphoinositides labelled with hydrogen isotopes are provided. In both approaches, the isotope atoms are introduced at a late stage in synthesis; this is desirable for radioactive isotope labels as it minimizes handling of radioactive materials. In one approach, the isotope label is introduced into a fully assembled phosphatidylinositol skeleton, and, in the second approach, an inositol derivative is labelled and then conjugated with the phosphatidyl residue.

In the first approach, suitable starting material is furnished by a preformed phosphoinositide wherein only one sec-OH is unprotected and available for reaction, while all other OH groups are blocked with temporary protecting groups, and, the phosphate residues may be blocked by temporary groups and present in phosphodiester or phosphotriester states. The key steps are outlined in Scheme 1 for the synthesis of 1D-1-(1',2'-O-dipalmitoyl-sn-glycero-3'-phospho)-myo-inositol-4,5-bisphosphate 9 (DPPtdIns-4,5-P$_2$) from 6 via the precursor 8 as a representative case.

Oxidation of 6 (Scheme 1, Step a) to the phosphatidyl-inosose 7 is carried out using CrO$_3$-pyridine or a related oxidation reagent. A hydrogen, deuterium or tritium atom is introduced (Step b) by reducing the ketone group of the phosphatidyl-inosose 7, using NaBH$_4$, NaB$^2$H$_4$ or NaB$^3$H$_4$ and equivalent reagents, to the corresponding secondary alcohol appearing respectively as H—C-2, $^2$H—C-2 or $^3$H—C-2 labelled 8 analogous with precursor 2. The product is purified to remove epimeric impurities, and subjected to deprotection (Step c); the reagents and protocols in Step c are chosen to suit the particular protecting group present in 6. In the specific case shown in Scheme 1, deprotection of benzyl groups is carried out by hydrogenolysis using H$_2$-Pd/C, and the target hydrogen isotope labelled phosphoinositide DPPtdIns-4,5-P$_2$ (9) obtained. DPPtdIns-3,4,5-P$_3$ is obtained by the same oxidation—reduction and deprotection sequence from the 3,4,5-tris(dibenzylphosphate) analogue of 6. DPPtdIns-3,4,5-P$_3$ is obtained also by the second approach discussed below.

Oxidation is carried out under the standard conditions for the chosen oxidizing reagent(s). Reduction is carried out preferably in a chloroform—NaHCO$_3$ buffer biphasic system with vigorous mixing; a phase transfer catalyst, e.g., Bu4NHSO$_4$, is a desirable adjunct.

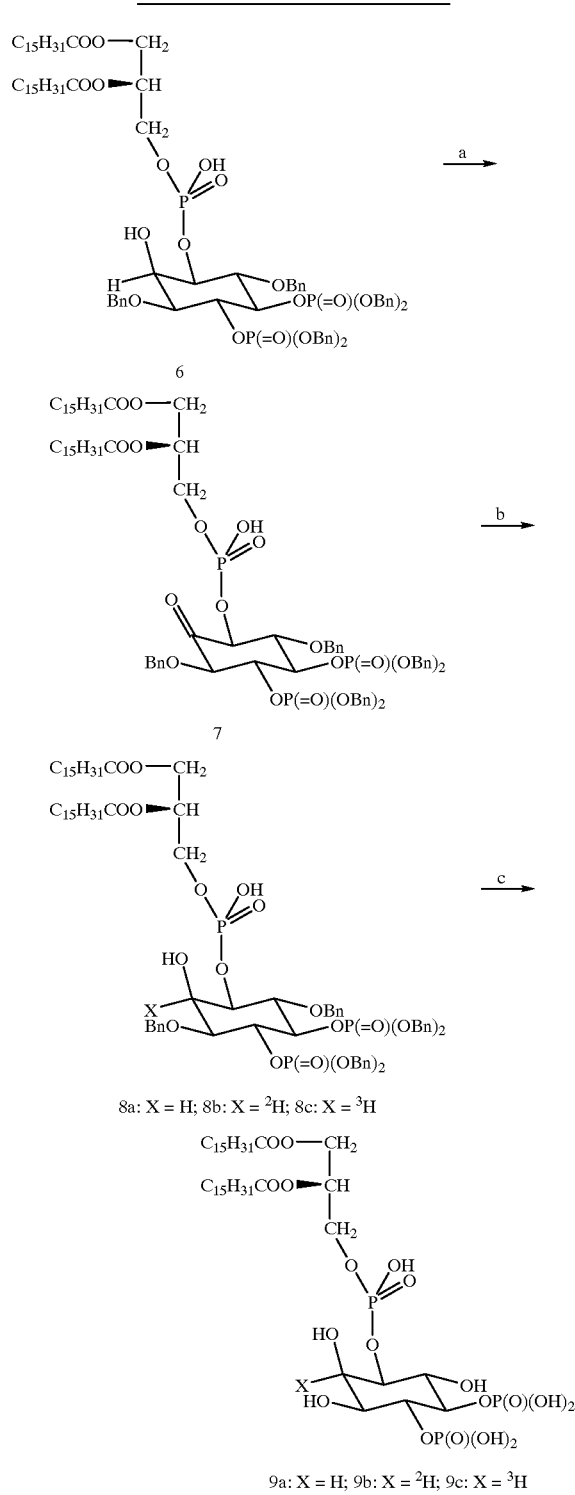

Scheme 1
Labeling of Preformed Phosphoinositide Derivative with Hydrogen Isotopes 8a: X = H; 8b: X = $^2$H; 8c: X = $^3$H 9a: X = H; 9b: X = $^2$H; 9c: X = $^3$H In the second approach, outlined in Scheme 2, a selectively protected myo-inositol, e.g., 1D-2,6-di-O-benzyl-myo-inositol-3,4,5-tris(dibenzylphosphate) 10, wherein only the equatorial 1-OH is unprotected, and all other OH groups are blocked with temporary protecting groups is a suitable starting material. Oxidation of 10 (Step a) to the corresponding inosose 11 is carried out using the reagent mixture comprising dimethylsulfoxide and acetic anhydride (DMSO-Ac$_2$O). A hydrogen, deuterium or tritium atom is introduced (Step b) by reduction of inosose 11, using NaBH$_4$, NaB$^2$H$_4$ or NaB$^3$H$_4$, to the corresponding secondary alcohol 12 carrying H—C—OH, $^2$H—C—OH or $^3$H—C—OH labels. The product is purified to remove epimeric impurities, and coupled (Step c) to a phosphatidyl residue using 1',2'-dipalmitoyl-sn-glycero-3'-phosphoric acid activated by triisopropylbenzenesulfonyl chloride (TPSCl) in pyridine. The purified product 13 is the labelled precursor analogous with 3, and is deprotected by H$_2$-Pd/C to labelled 1D-1-(1',2'-O-dipalmitoyl -sn-glycero-3'-phospho)-myo-inositol-3,4,5-trisphosphate (DPPtdIns-3,4,5-P$_3$) 14.

Scheme 2
Synthesis of Labelled DPPtdIns-3,4,5-P$_3$: X = H, $^2$H or $^3$H

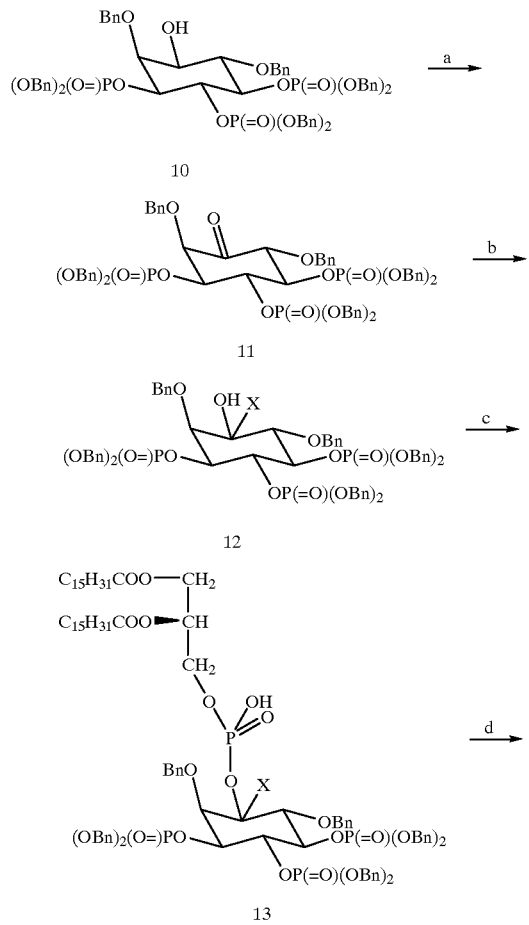

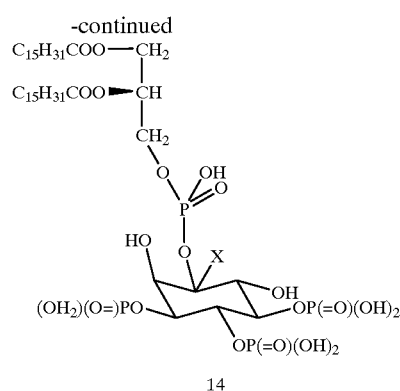

14

The phosphatidyl-inosose (7) and inosose (11) employed in Scheme 1 and 2 respectively are important novel intermediates. Equally useful are the 2-phosphatidyl-1-keto and 1-phosphatidyl-6-keto structural isomers of 7 and the 2-keto and 6-keto isomers of 11 prepared by oxidation of the corresponding 1-phosphatidyl-1-OH and 1-phosphatidyl-6-OH compounds. Both phosphatidyl-inosose and inosose types may have temporary protecting groups other than benzyls so as to avoid metal catalyzed hydrogenolysis for deprotection and concomitant reduction of C—C unsaturation in the fattyacyl chains. The present invention discloses novel selectively protected chiral myo-inositol synthons that incorporate temporary protecting groups which are removed without metal catalyzed hydrogenation. In addition, the groups are compatible with the reagents and conditions validated in Schemes 1 and 2 for the oxidation and reduction steps.

Any suitable method may be employed for the preparation of the starting materials required for conversion into the key phosphatidyl-inosose and inosose intermediates in Schemes 1 and 2. Compound 6 leading to the synthesis of PtdIns-4,5-P$_2$ was prepared from 1D-3,6-di-O-benzyl-myo-inositol-4,5-bis(dibenzylphosphate) (Toker A., et al., 1994, J. Biol. Chem., 269: 32358) by phosphatidylation using 1',2'-dipalmitoyl-sn-glycero-3'-phosphoric acid activated by tri-isopropylbenzenesulfonyl chloride (TPSCl) in pyridine as shown in Scheme 2 for the related case of labelled inositol derivative 12. This type of methodology is not available in the prior art for the preparation of the D-3-phosphorylated series of phosphoinositides, but is disclosed now as outlined later in Schemes 3, 4, and 5. The selectively protected myo-inositol 10 used in Scheme 2 for the synthesis of labelled PtdIns-3,4,5-P$_3$, was prepared by our approach for unambiguous synthesis (Aneja, S. G., et al., 1997, Tetrahedron Lett. 38: 803–806); other selectively protected myo-inositol synthons appropriate for labeling are prepared by the same method.

Novel Synthesis of the Phosphoinositides

The synthesis of PtdIns-3,4,5-P$_3$ was carried out (Scheme 3) from 1B-1,2:4,5-di-O-cyclohexylidene-6-O-benzyl-myo-inositol (−)-17 as the key optically resolved synthon, which was prepared as follows. Optically pure 1D-1,2:4,5-di-O- cyclohexylidene-myo-inositol (–)-15, and its 3,6-di-O-benzyl derivative (–)-16, were prepared as described in our recent communication (Aneja, R., et al., 1995, Tetrahedron Asymmetry, 6: 17). Hydrogen transfer reaction using $NH_4^+$ $HCOO^-$/Pd-C in boiling methanol caused selective mono-debenzylation of (–)-16 to yield 1D-6-O-benzyl derivative (–)-17, $[\alpha]_D$ –55.3° (c 0.5, $CHCl_3$). The absolute stereochemistry of (–)-17 follows from that established for (–)-28 by correlation with 1D-1,4,5,6-tetra-O-benzyl-myo-inositol (Aneja, R., et al., 1995, Tetrahedron Asymmetry, 6: 17), an established reference for stereochemical assignments in the myo-inositol series (Aneja, R. and Parra, A., 1994, Tetrahedron Lett., 35: 525).

Selective removal of the 4,5-O-cyclohexylidene residue by treatment of (–)-17 with ethylene glycol and catalytic p-TSA in $CH_2Cl_2$—$CH_3CN$ under kinetic control gave (–)-18, $[\alpha]_D$ –7.95° (c 1.0 $CHCl_3$). Evidence proving that the cyclohexylidene group had not migrated to the 2,3-O-position was provided by alternative preparation of (–)-18 as follows. Reaction of (–)-17 with BzCl/Py formed the 3-O-benzoyl derivative (+)-19, $[\alpha]_D$ +5.5° (c 1.1, $CHCl_3$); removal of 4,5-O-cyclohexylidene residue, and alkaline hydrolysis of the 3-O-Bz ester gave a product identical with (–)-18. Reaction of (–)-18 successively with dibenzyl N,N-di-isopropylphosphoramidite and m-chloroperoxybenzoic acid yielded the 3,4,5-tris-(dibenzylphosphate) derivative, (–)-20 $[\alpha]_D$ –5.5°, (c 1.1, $CHCl_3$). Treatment of (–)-20 with NaI in acetone at 40° C. to effect selective anionic debenzylation to the tris-monobenzylphosphate 21, followed by acid catalyzed hydrolytic removal of the 1,2-O-cyclohexylidene protecting group by treatment of 21 with acetic acid-water (80:20) at 95° C. yielded (+)-23. The treatment of (+)-23 with phenyldiazomethane (CAUTION: carcinogenic and may explode) yielded (+)-22 which was obtained directly from (–)-20, albeit in lower yield.

Scheme 3 Synthesis of DPPtdIns-3,4,5-$P_3$

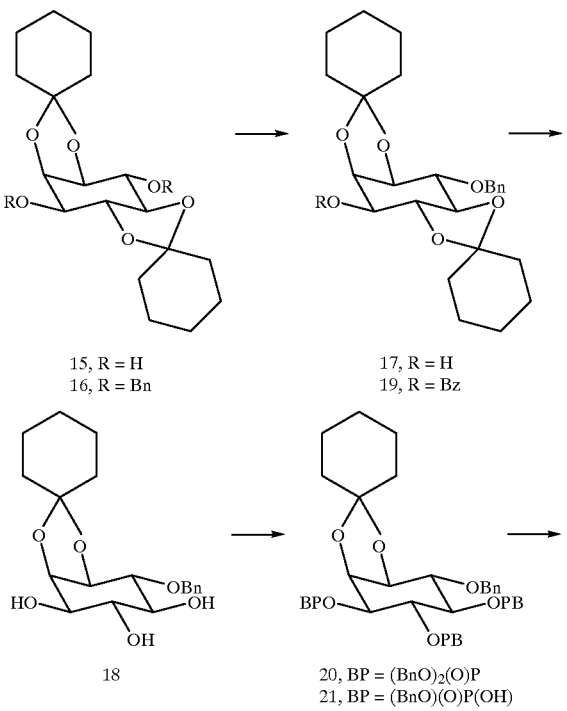

15, R = H
16, R = Bn

17, R = H
19, R = Bz

18

20, BP = $(BnO)_2(O)P$
21, BP = $(BnO)(O)P(OH)$

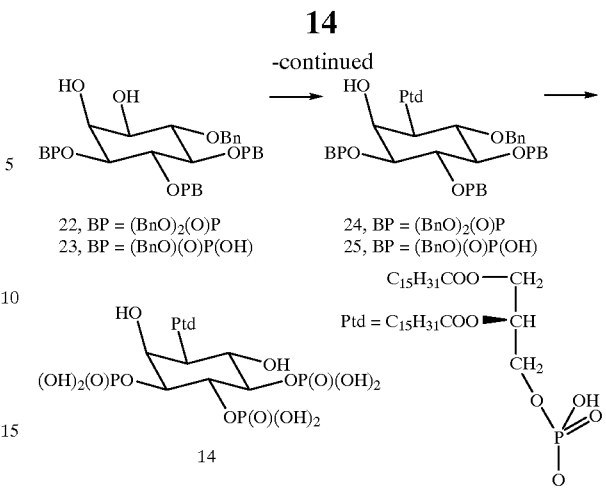

22, BP = $(BnO)_2(O)P$
23, BP = $(BnO)(O)P(OH)$

24, BP = $(BnO)_2(O)P$
25, BP = $(BnO)(O)P(OH)$

14

Reaction of the 1,2-diol synthon 22 with the phosphatidic acid 1',2'-O-dipalmitoyl-sn-glycero-3'-phosphoric acid (DPPtdA) is carried out in anhydrous pyridine using TPSCl as the condensing agent, by the general protocol described for phosphodiester synthesis (Aneja, R. et al., 1970, Biochim. Biophys. Acta, 218: 102–111). The product 24 of regioselective phosphatidylation of the 1D-1-OH is a key late stage intermediate for (1) deprotection to DPPtdIns-3, 4,5-$P_3$ non-labelled 14, and (2) oxidation—reduction as in Scheme 1 leading to hydrogen isotope labelled DPPtdIns-3,4,5-$P_3$ 14. Deprotection by complete debenzylation is effected by Pd catalyzed hydrogenation.

The phosphatidylation reaction applied to the 1,2-diol system in myo-inositol derivatives gives the 1-phosphatidyl as the major product (e.g., 24) and a smaller amount of the 2-phosphatidyl derivative. Both products were characterized fully in the phosphatidylation reaction for the synthesis of DPPtdIns-4,5-$P_2$ and were described earlier in this Specification. The 1D-1-Phosphatidyl isomer was utilized as the starting material 6 in Scheme 1, and the 1D-2-phosphatidyl isomer was ascribed structure 5 as an isotope labelled key precursor.

Complete, and, selective partial benzylation of (–)-18 generate tetra-, tri- and di-O-benzylated intermediates. Each of these intermediates is subjected to the reaction sequence shown in Scheme 3 for (–)-18 for the synthesis of the complete series comprising phosphatidyl-myo-inositol and derived sets of structurally isomeric mono and diphosphates.

Useful variations are made in Scheme 3 by using temporary protecting groups other than benzyls and this avoids metal catalyzed hydrogenolysis for deprotection and concomitant undesirable reduction of C—C unsaturation in the fattyacyl chains. The overall strategic sequence of reactions employed in Scheme 3 is retained. Representative protecting groups for the OH and the phosphate residues are illustrated in Schemes 4 and 5. The novel selectively protected chiral myo-inositol synthons shown incorporate protecting groups that are benign to C—C multiple bonds, provide adequate protection during the 2-OH oxidation reduction sequence validated in Scheme 1 for labeling with hydrogen isotopes, and are removed without jeopardy to the rest of the phosphoinositide structure.

Examples and methods for preparation shown in Scheme 4 and 5 include but are not limited to 4-methoxybenzyl, the various chloroacetyl, butanoyl and levulinoyl for OH, and 4-methoxybenzyl, fluorenylmethyl, and trichloroethyl for phosphate.

Reaction (Scheme 4) of optically pure 1D-1,2:4,5-di-O-cyclohexylidene-myo-inositol (–)-15 with 4-methoxybenzyl chloride (PMBCl) and NaH gave the following derivatives: 1D-1,2:4,5-di-O-cyclohexylidene-3,6-di-O-PMB-myo-inositol (−)-26, [α]$_D$−68.8° (c 1.1, CHCl$_3$), 1D-1,2:4,5-di-cyclohexylidene-3-O-PMB-myo-inositol (38, Scheme 5), [α]$_D$−41.92° (c 1.1, CHCl$_3$), and 1D-1,2:4,5-di-O-cyclohexylidene-6-O-PMB-myo-inositol (−)-27, [α]$_D$−57.96° (c 1.1, CHCl$_3$). Selective removal of the 4,5-O-cyclohexylidene residue by treatment of (−)-27 with ethylene glycol and catalytic p-TSA in CH$_2$Cl$_2$—CH$_3$CN under kinetic control gave 1D-2-O-cyclohexylidene-6-O-PMB-myo-inositol (−)-28, [α]$_D$−2.58°, (c 1.0 CHCl$_3$). Evidence proving that the cyclohexylidene group had not migrated to the 2,3-O-position was provided by alternative preparation of (−)-28 as follows. Reaction of (−)-27 with BzCl/Py formed 1D-3-O-benzoyl-1,2:4,5-di-O-cyclohexylidene-6-O-PMB-myo-inositol (−)-29, [α]$_D$−0.31° (c 1.1, CHCl$_3$); removal of 4,5-O-cyclohexylidene residue, and alkaline hydrolysis of the 3-O-Bz ester gave a product identical with (−)-28. The phosphorylation steps is carried out with di-(9-fluorenylmethyl) N,N′-diisopropylphosphoramidite prepared as described (Watanabe, Y., et al., 1997, Tetrahedron Lett., 38:. 7407), and the two fluorenylmethyl protecting groups on phosphates are removed consecutively by anionic debenzylation with NaI in boiling acetone and NET$_3$ at r.t., and oxidative removal of the PMB groups is effected by 2,3-dicyano-5,6-dichlorobenzoquinone (DDQ). Phosphatidylation employs 1′-O-stearoyl-2′-O-arachidonyl-sn-glycero-3′-phosphoric acid 36 (SAraPtd: R′=stearoyl; R″=arachidonyl). A novel synthesis of this phosphatidic acid is described later in this Specification; the method is suitable for all mixed acid phosphatidic acids of the type 1′-O-fattyacyl′-2′-O-fattyacyl″-sn-glycero-3′-phosphoric acid.

Complete, and, selective partial 4-methoxybenzylation of 1D-1,2-O-cyclohexylidene-6-O-PMB-myo-inositol (−)-28 generate tetra-, tri- and di-(4-methoxybenzyl) derivatives. Each of these intermediates is subjected to the reaction sequence shown in Scheme 4 for (−)-18 for the synthesis of to obtain the corresponding stearoyl-arachidonyl based phosphatidyl-myo-inositol(phosphates).

Scheme 4 Synthesis of SAraPtdIns-3,4,5-P$_3$

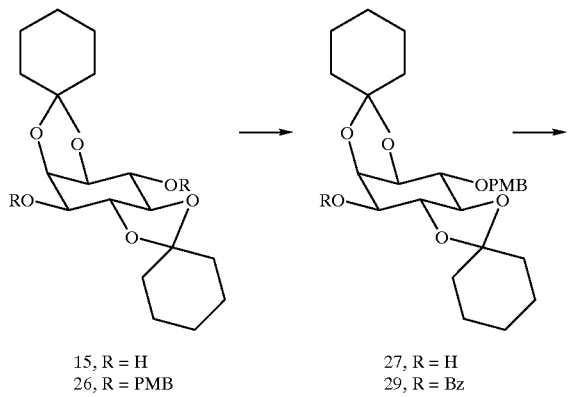

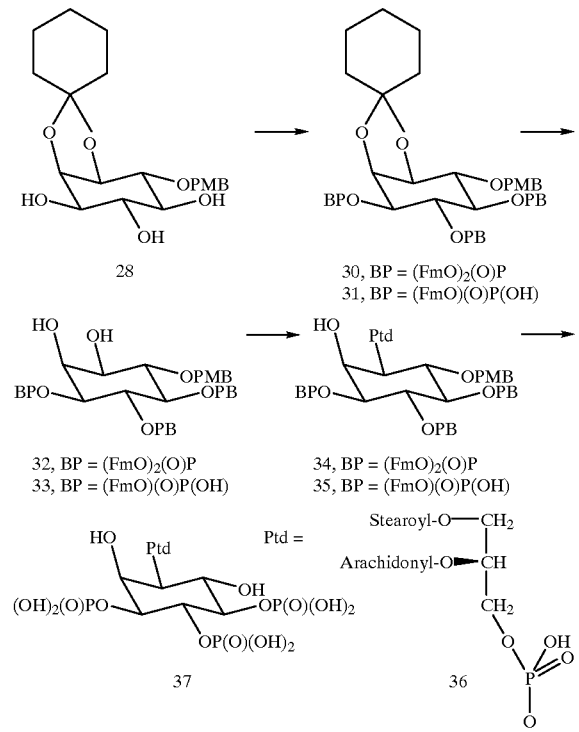

Synthesis using another set of temporary protecting groups is employed in Scheme 5. Methoxybenzylation of optically pure 1D-1,2:4,5-di-O-cyclohexylidene-myo-inositol (−)-15 gave 1D-1,2:4,5-di-O-cyclohexylidene-3-O-PMB-myo-inositol (−)-38, [α]$_D$−55.78° (c 1.0, CHCl$_3$). Reaction of (−)-38 with trichloroacetyl chloride in the presence of pyridine gave the 6-O-ester 1D-1,2:4,5-di-O-cyclohexylidene-3-O-PMB-6-O-trichloroacetyl-myo-inositol (−)-39, [α]$_D$−40.46° (c 1.08, CHCl$_3$). Selective removal of the 4,5-O-cyclohexylidene is effected by transketalization of 39 under kinetic control to obtain 40, and the PMB protection is removed by reaction of the 4,5-diol 40 with moist DDQ. The resulting 3,4,5-triol 41 is converted into the tris-phosphotriester derivative 42 using the one pot two step phosphitylation—oxidation chemistry. The phosphitylation reagent O-benzyl-O-trichloroethyl-N,N-diisopropylphosphoramidite is prepared by a general procedure for dialkylphosphoramidites (Bannwarth, W. and Trzeciak, A., 1987, Helv. Chim. Acta., 70: 175). The reaction between 41 in anhydrous CH$_2$Cl$_2$, the phosphoramidite and 1H-tetrazole is carried out at sub-zero to room temperature, and the oxidation with m-chloro-peroxybenzoic acid (m-CPBA) is performed at −70 to −40° C. to obtain 42. Removal of the 1,2-di-O-cyclohexylidene protecting group of 42 is effected by treatment with methanol and trifluoroacetic acid in CH$_2$Cl$_2$ at ice bath temperature to form 1$_D$- 6-0-trichloroacetyl-myo-inositol-3,4,5-tris(benzyl-trichloroethylphosphate) 44. Anionic debenzylation of the phosphotriesters in 42 is carried out by reaction with NaI in hot acetone to form 1D-6-O-trichloroacetyl-myo-inositol-3,4,5-tris(monotrichloroethylphosphate) 43 (structure not shown) as an alternative synthon for phosphatidylation. Phosphatidylation is performed as described for 22 and 32 (Schemes 3 and 4), and trichloroacetyl and trichloroethyl protecting groups are removed by reaction with activated zinc, AcOH and Py (Yamamura, S., 1968, Chem. Comm., 1494) to obtain target SAraPtdIns-3,4,5-P$_3$.

Scheme 5
Synthesis of 1D-6-O-trichloracetyl-myo-inositol-3,4,5-tris(trichloroethylphosphate)44

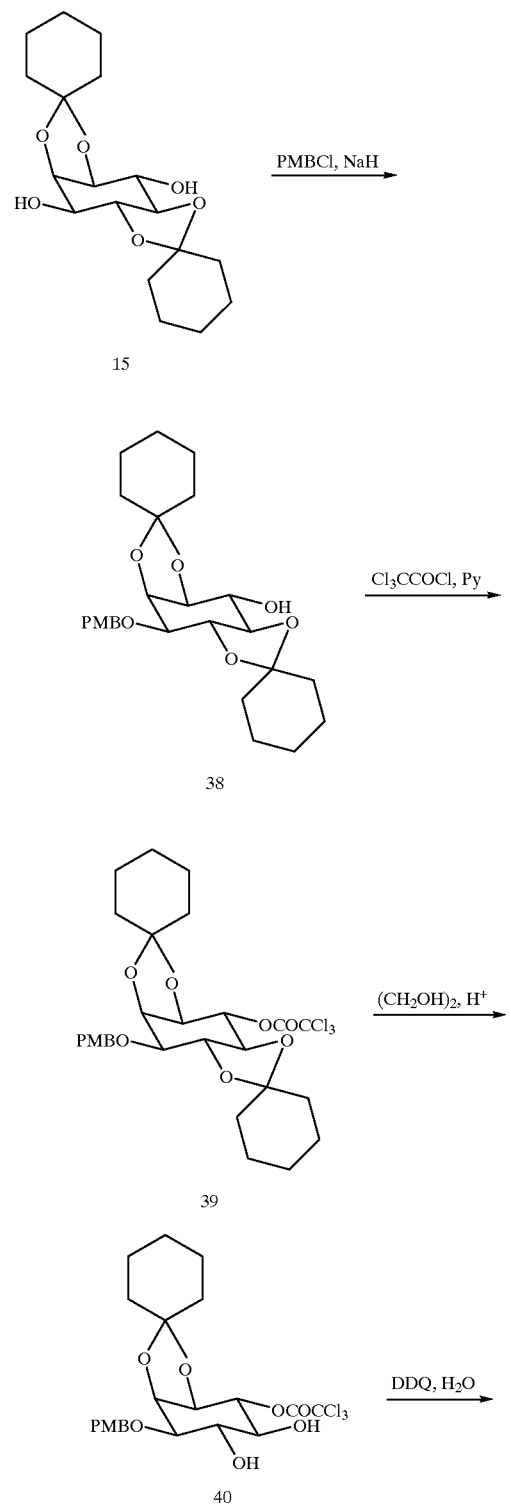

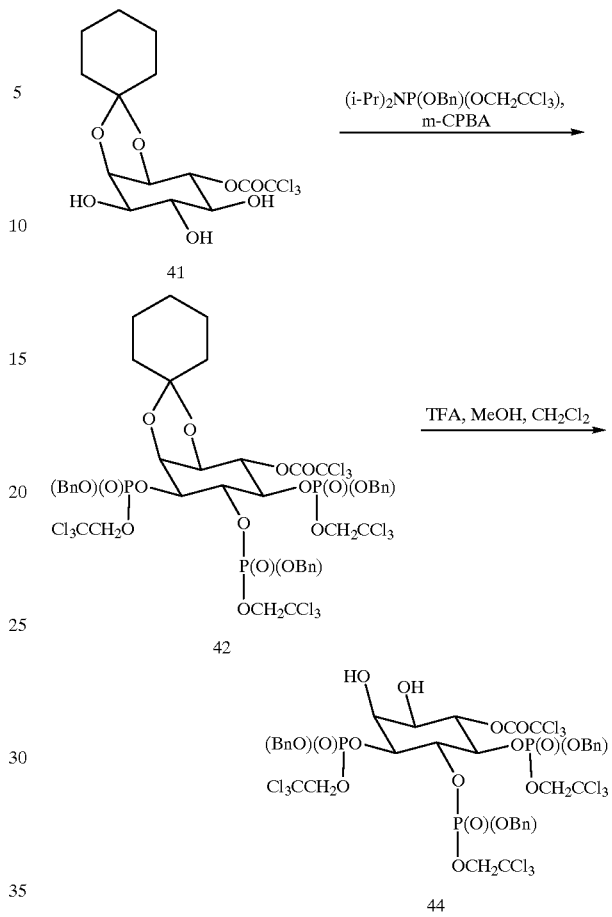

1D- 1-(1'-O-stearoyl-2'-O-arachidonyl-sn-glycero-3'-phosphoric acid(48), used in Schemes 4 and 5, was prepared by a novel method outlined in Scheme 6. 1', 2'-Di-O-stearoyl-sn-glycero-3'-phosphoric acid was esterified with n-butanol in anhydrous pyridine treated with TPSCl. The resulting 1', 2'-di-O-stearoyl-sn-glycero-3'-phosphate-n-butyl ester (DSPA-n-Bu, 45), in ether-boric acid buffer was treated with phospholipase A$_2$ (PLA$_2$) from *Crotalus adamanteus* venom and purified to obtain 1'-O-stearoyl-sn-glycero-3'-phosphate-n-butyl ester (46). The product was esterified to n-butyl-1'-O-stearoyl-2'-O-arachidonyl-sn-glycero-3'-phosphate (47) using an excess of arachidonic acid, DCC and DMAP in anhydrous CCl$_4$-CH$_2$Cl$_2$. Hydrolysis of 47 in buffer pH 8.5 at 37° C. catalyzed by phospholipase D (PLD) from *Streptomyces chromofuscus* yielded the required 1'-O-stearoyl-2'-O-arachidonyl-sn-glycero-3'-phosphoric acid (48). With alternative alkyl esters, e.g. tert-butyl ester of DSPA, acid catalyzed hydrolysis is used in place of PLD. This method is applicable for other mixed acid 1'-saturated fattyacyl-2'-unsaturated fattyacyl type phosphatidic acids. The method is advantageous over lipolysis of DSPA and esterification of the resulting lysoDSPA wherein poor solubilities in reaction media and precipitation as Ca$^{2+}$ salts reduce reaction rates and allow acyl migration to become competitive side reactions.

Scheme 6
Synthesis of 1-O-stearoyl-2-O-arachidonyl-sn-glycero-3-phosphoric acid 48

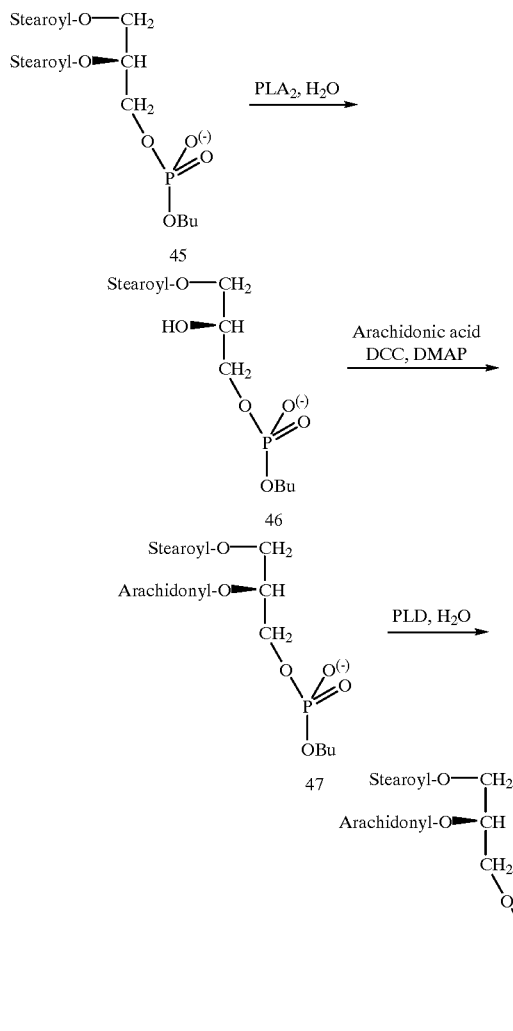

for reaction at the equatorial 1-OH. Products with identical structures were obtained by esterification of the 1- and 2-phosphatidyl isomers produced in the phosphodiester condensation. Specifically, reaction between 1D-1-(1',2'-O-dipalmitoyl-sn-glycero-3'-phospho)-3,6-di-O-benzyl-myo-inositol-4,5-bis(dibenzylphosphate) 6 and phenyldiazomethane (CAUTION) gave its benzyl ester 49.

Scheme 7 Preparation of Phosphatidyl-inosose esters

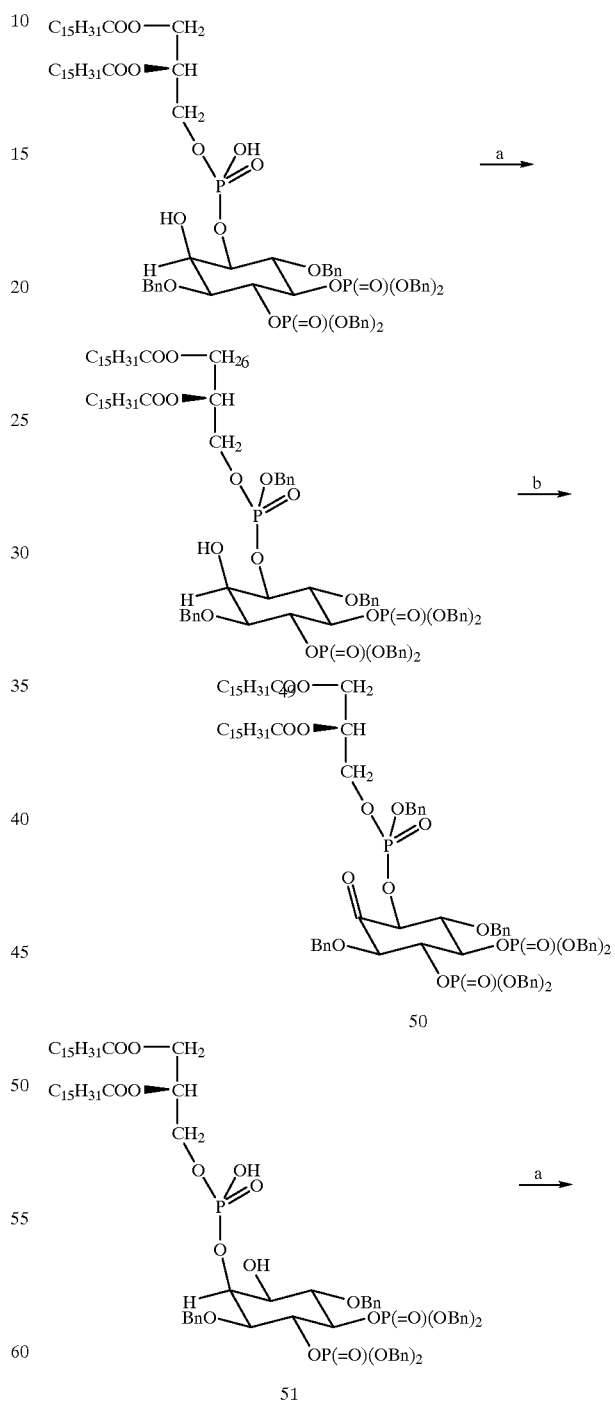

In the syntheses described herein, the phosphodiester condensation forms the 1- as well as the 2-phosphatidyl ester products. A novel alternative allows more selective reaction at the equatorial 1-OH. In an initial reaction with dibutyltin oxide in refluxing methanol, followed by complete drying in a vacuum, the dibutylstannylene derivative of the 1,2-diol group is obtained. It is dissolved in an inert solvent and treated at sub zero temperature with $NET_3$ followed by a dropwise addition of an ether solution of benzyl-1',2'-diacyl-sn-glycerophosphochloridate. This phosphochloridate reagent is prepared in two steps: (i) esterification of phosphatidic acid with benzyl alcohol (as in Scheme 6), followed by (ii) reaction with oxalyl chloride or equivalent chlorinating reagent. The major product, purified by chromatography, is the 1-phosphatidyl-myo-inositol benzyl ester, together with a minor amount of the 2-phosphatidyl-myo-inositol benzyl ester; inclusion of CsF in the reaction prior to addition of the phosphochloridate improves the selectivity

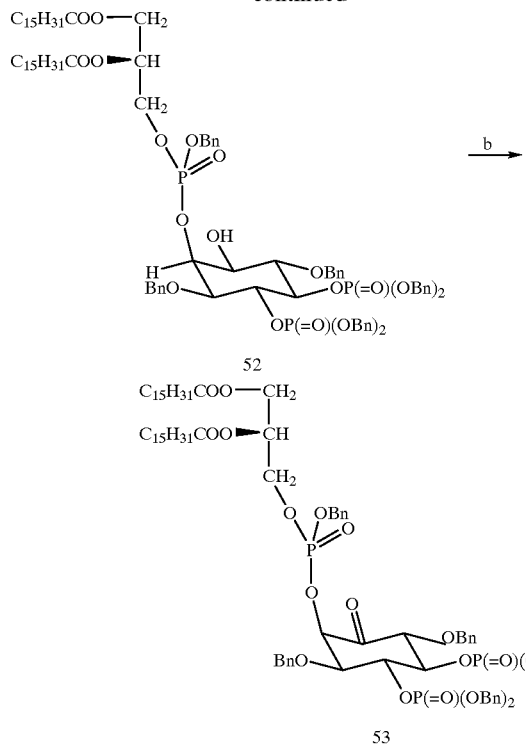

Similarly, the 2-phosphatidyl isomer 1D-2-(1',2'-O-dipalmitoyl-sn-glycero-3'-phospho)-3,6di-O-benzyl-myo-inositol-4,5-bis(dibenzylphosphate) 51 was esterified to 52. Both 49 and 52 formed on oxidation the corresponding inosose derivative, 50 and 53 respectively. These phosphatidyl-inosose esters represent another group of key intermediates for labeling with hydrogen isotopes.

In the present synthesis, (protected)phosphates 'can be introduced at the myo-inositol 3-, 4- or 5- positions in separate steps using $^{31}$P and $^{32}$P forms of the same dialkyloxy-dialkylamino-phosphoramidite. Thus phosphoinositides can be prepared which are labelled with $^{32}$P-phosphate or $^{35}$S-thiophosphate group at a selected site while non-labelled phosphates are at other locations. Such selectively labelled materials are important for studies of phosphoinositide-phosphate phosphatases. The ability to effect selective phosphorylation in separate steps is engendered by the high reactivity of 3-O-PMB groups compared with the 6-O-PMB. For instance, reaction between 1D-1,2:4,5-Di-O-cyclohexylidene-3,6-di-O-PMB-myo-inositol (−)-26 and one equivalent of DDQ caused selective removal of the 3-O-protection. The deprotected OH is thus amenable to reaction including phosphorylation. Because oxidative rather than reductive deprotection is employed, the present synthesis via O-PMB protection is applicable for the synthesis of $^{35}$S-thiophosphates.

The synthetic methods disclosed herein are applied also to the 1L- or DL- myo-inositol derivatives in addition to the 1D-series shown in Schemes 1 to 5, and each condensed with phosphatidic acid with sn-glycero-1- or rac-glycero-⅓- configurations in addition to the sn-glycero-3- in Scheme 6. Further, various inositol and phosphatidic acids types are cross coupled. Moreover, phosphatidic acids carrying saturated and unsaturated fattyacyl, alkyl, and sphingolipid residues are applied. Thus these methods provide a diversity of structures with the phosphoinositide motif in non-labelled and labelled forms, important labelled precursors of the latter and key intermediates for introducing labels. It is emphasized that the descriptions herein and in the examples are merely illustrative of the invention as defined in the claims. The chemistry and protocols for products with and without isotope labels are identical and hence ordinarily skilled practitioners will understand that synthesis of either type of product is sufficient validation of the novel methodology for both labelled and non-labelled type phosphoinositides.

EXAMPLES

General Procedures

The progress of reactions was monitored by thin layer chromatography on silicagel G plates. Final products were judged to be <99% pure. Satisfactory MS (E. S., MALDI-TOF) and $^1$H NMR (400 MHz) data conforming to the assigned structure were obtained for all compounds.

Oxidation of sec. Alcohol to Ketone; Procedure A: With Pyridinium Dichromate ($CrO_3.Py_2$)

Chromium trioxide (60.0 mg) is added to stirred solution of anhydrous pyridine (95 mg) in anhydrous dichloromethane (1 ml) under $N_2$ gas blanket. After mixing for 15 min., a solution of the sec. alcohol (20.0 mg) in anhydrous dichloromethane (0.2 ml) is added. Reaction times ranged from 2 to 10 minutes at r.t. After quenching with ice cold aqueous $SO_2$, the crude product is recovered by evaporation of the organic layer, and purified by chromatography on flash silica using a gradient of $CHCl_3$—MeOH—$NH_4OH$.

Oxidation of sec. Alcohol to Ketone; Procedure B: DMSO/$Ac_2O$

The sec. alcohol (10.0 mg) is added to a 3:2 mixture of DMSO/$Ac_2O$ (0.5 ml). The reaction is stirred at 35–40° C. for 4 hr. and poured into ice cold aqueous $NaHCO_3$ solution. The crude is extracted into dichloromethane, washed with water, recovered by evaporation, and purified by chromatography on flash silica using a gradient of $CHCl_3$—MeOH—$NH_4OH$.

Reduction with $NaBH_4/NaB^2H_4$

A solution of the ketone (2 mg) (phosphatidyl-inosose, inosose) in chloroform is mixed vigorously (Vortexed) with $NaBH_4$ (1 equivalent, added in fractional lots) in aqueous $NaHCO_3$. The layers are separated, the product recovered from the organic layer, and purified by chromatography on flash silica using a gradient of $CHCl_3$—MeOH—$NH_4OH$. The same procedure is followed with $NaB^2H_4$ dissolved in $^2H_2O$ containing $Na^2HCO_3$. Experiments with $NaB^3H_4$ in tritiated water are conducted in the Radiochemical facility under the guidance of the Safety Committee.

Example 1

1D-1-(1',2'-O-dipalmitoyl-sn-glycero-3'-phospho),-3, 6,di-O-benzyl-2-myo-inosose-4,5-bis (dibenzylphosphate) 7

Oxidation of 1D-1-(1',2'-O-dipalmitoyl-sn-glycero-3'-phospho)-3,6-di-O-benzyl-myo-inositol-4,5-bis (dibenzylphosphate) 6 by $CrO_3.Py_2$ (Procedure A) at r.t. for 5 min was quenched by ice cold aqueous $SO_2$. The product recovered by evaporation of the organic layer. Purification by chromatography on flash silica using a gradient of $CHCl_3$—MeOH—$NH_4OH$ gave 1D-1-(1', 2'-O-dipalmitoyl-sn-glycero-3'-phospho)-3,6-di-O-benzyl-2-myo-inosose-4, 5-bis(dibenzylphosphate) 7 (yield 69%).

Example 2

1D-2-(1',2'-O-dipalmitoyl-sn-glycero-3'-phospho)-3, 6-di-O-benzyl-1-myo-inosose-4,5-bis (dibenzylphosphate)

Oxidation of 1D-2-(1',2'-O-dipalmitoyl-sn-glycero-3'-phospho)-3,6-di-myo-inositol-4,5-bis(dibenzylphosphate)

51 by Procedure A was complete at r.t. in min; worked up and purification as in Example 1, gave 1D-2-(1',2'-O-dipalmitoyl-sn-glycero-3'-phospho)-3,6-di-1-myo-inosose-4,5-bis(dibenzylphosphate) (yield 86%).

Example 3

1D-2,6-di-O-benzyl-1-myo-inosose-3,4,5-tris (dibenzylphosphate)

Oxidation of 1D-2,6-di-O-benzyl-myo-inositol-3,4,5-tris (dibenzylphosphate) 10

By Procedure B: Oxidation, work up and purification as in the general protocol gave 1D-2,6-di-O-benzyl-1-myo-inosose-3,4,5-tris(dibenzylphosphate) 11 (yield 78%).

Example 4

1D-1-(1',2'-O-dipalmitoyl-sn-glycero-3'-phospho)-3,6-di-benzyl-myo-inositol-4,5-bis (dibenzylphosphate)-benzyl ester 49

A chloroform of 1D-1-(1',2'-O-dipalmitoyl-sn-glycero-3'-phospho)-3,6-di-O-benzyl-myo-inositol-4,5-bis (dibenzylphosphate) 6 was washed with ice cold aqueous hydrochloric acid (0.1 M), and treated with a chloroform solution of phenyldiazomethane (excess; CAUTION: carcinogen and explosion hazard). Purification by chromatography on silica gave the phosphotriester product 1D-1-(1',2'-O-dipalmitoyl-sn-glycero-3'-phospho)-3,6-di-O-benzyl-myo-inositol-4,5-bis(dibenzylphosphate)-benzyl ester 49 (yield 89%).

Example 5

1D-2-(1',2'-O-dipalmitoyl-sn-glycero-3'-phospho)-3,6-di-O-benzyl-1-myo-inosose-4,5-bis (dibenzylphosphate)-benzyl ester 52

Reaction between 1D-2-(1',2'-O-dipalmitoyl-sn-glycero-3'-phospho)-3,6-di-O-benzyl-myo-inositol-4,5-bis (dibenzylphosphate) 51 with phenyldiazomethane as in Example 4 and purification by chromatography gave the pure phosphotriester product 1D-2-(1',2'-O-dipalmitoyl-sn-glycero-3'-phospho)-3,6-di-O-benzyl-1myo-inosose-4,5-bis (dibenzylphosphate)-benzyl ester 52 (yield 91%).

Example 6

1-(1',2'-O-dipalmitoyl-sn-glycero-3'-phospho)-3,6-di-O-benzyl-2-myo-inosose-4,5-bis (dibenzylphosphate)-benzyl ester 50

Oxidation of 1D-1-(1',2'-O-dipalmitoyl-sn-glycero-3'-phospho)-3,6-di-O-benzyl-myo-inositol-4,5-bis (dibenzylphosphate)-benzyl ester 49 using Procedure A, and purification as in the general protocol gave 1D-1-(1',2'-O-dipalmitoyl-sn-glycero-3'-phospho)-3,6-di-O-benzyl-2myo-inosose-4,5-bis(dibenzylphosphate)-benzyl ester 50 (yield 65%).

Example 7

1D-2-(1',2'-O-dipalmitoyl-sn-glycero-3'-phospho)-3,6-1myo-inosose-4,5-bis(dibenzylphosphate)-benzyl ester 53

Oxidation of 1D-2-(1',2'-O-dipalmitoyl-sn-glycero-3'-phospho)-3,6-di-O-benzyl-myo-inositol-4,5-bis (dibenzylphosphate)-benzyl ester 52 by Procedure A, work up and purification as in the general protocol gave 1D-2-(1',2'-O-dipalmitoyl-sn-glycero-3'-phospho)-3,6-di-O-benzyl-1-myo-inosose-4,5-bis(dibenzylphosphate)-benzyl ester 53 (yield 72%).

Example 8

1D-1-(1',2'-O-dipalmitoyl-sn-glycero-3'-phospho)-3,6-di-O-benzyl-myo-inositol-4,5-bis (dibenzylphosphate) 6

$NaBH_4$ Reduction of 1D-1-(1',2'-O-dipalmitoyl-sn-glycero-3'-phospho)-3,6-di-O-benzyl-2-myo-inosose4,5-bis (dibenzylphosphate) 7 by the general protocol of Procedure C gave the product 8a(x=H) identical with 1D-1-(1',2'-O-dipalmitoyl-sn-glycero-3'-phospho)-3,6-di-O-benzyl-myo-inositol-4,5-bis(dibenzylphosphate) 6(yield 45%).

Example 9

1D-1-(1',2'-O-dipalmitoyl-sn-glycero-3'-phospho)-3,6-di-O-benzyl-myo-inositol-4,5-bis (dibenzylphosphate),$D_1$8b $NaB^2H_4$ Reduction of 1D-1-(1',2'-O-dipalmitoyl-sn-glycero-3'-phospho)-3,6-di-O-benzyl-2-myo-inosose-4,5-bis(dibenzylphosphate) 7 was carried out by Procedure C, in solvent $D_2O$ containing $NaDCO_3$ as a buffering salt, worked up and purified as in the general protocol. The product was characterized by MS data as the mono-deuterated derivative 1D-1-(1',2'-O-dipalmitoyl-sn-glycero-3'-phospho)-3,6-di-O-benzyl-myo-inositol-4,5-bis(dibenzylphosphate),$D_1$8b (yield 41%).

Example 10

1D-2-(1',2'-O-dipalmitoyl-sn-glycero-3'-phospho)-3,6-di-O-benzyl-myo-inositol-4,5-bis (dibenzylphosphate)51

$NaBH_4$ reduction of 1D-2-(1',2'-O-dipalmitoyl-sn-glycero-3'-phospho)-3,6-di-O-benzyl-1-myo-inosose-4,5-bis (dibenzylphosphate) by Procedure C, involving reduction, work up and purification as in the general protocol, gave product identical with 1D-2-(1',2'-O-dipalmitoyl-sn-glycero-3'-phospho)-3,6-di-O-benzyl-myo-inositol-4,5-bis (dibenzylphosphate) 51 (yield 34%); a companion product (yield 43%) was identified by MS as a mono-debenzylated derivative of 51.

Example 11

1D-2-(1',2'-O-dipalmitoyl-sn-glycero-3'-phospho)-3,6-di-O-benzyl-1-myo-inosose-4,5-bis (dibenzylphosphate)-$D_1$ $NaB^2H_4$ reduction of 1D-2-(1',2'-O-dipalmitoyl-sn-glycero-3'-phospho)-3,6-di-O-benzyl-1-myo-inosose-4,5-bis(dibenzylphosphate) by Procedure C was carried out in $D_2O$ as in Example 9. The pure product (yield 48%) was identified by MS as 1D-2-(1',2'-O-dipalmitoyl-sn-glycero-3'-phospho)-3,6-di-O-benzyl-1-myo-inosose-4,5-bis (dibenzylphosphate)-$D_1$.

Example 12

Isomerization of 1D-2-(1',2'-O-dipalmitoyl-sn-glycero-3'-phospho)-3,6-di-O-benzyl-1-myo-inosose-4,5-bis(dibenzylphosphate) 51

A solution of 51 (30.3 mg) in anhydrous pyridine (0.3 ml) was treated with triisopropyl-benzene sulfonyl chloride (TPSCl) (2.3 mg) and left at r.t. for 2 hr. The temperature was dropped to 0–5° and water (1 drop) added, and left at r.t. for 3 hr. TLC showed the formation of a mixture of the starting 51 and its 1-phosphatidyl isomer 6 (45:55) from which 6 was obtained pure by chromatography on silica.

What is claimed:

1. A substantially purified phosphoinositide compound that comprises at least a first stable or radioactive isotope label within the inositol or glycerol residue of said phosphoinositide compound; wherein said stable or radioactive isotope label is selected from the group consisting of $^2H$, $^3H$, $^{32}P$, $^{33}P$ and $^{35}S$ and wherein said phosphoinositide compound has the myo-inositol-based structure:

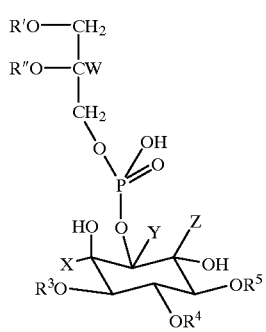

wherein:

R',R''=fattyacyl, alkyl or H;
$R^3$, $R^4$, $R^5$=H or $Q(T)(OH)_2$;
Q=P, $^{32}P$ or $^{33}P$;
T=O or $^{35}S$;
W, X, Y, Z=$^2H$, $^3H$ or H; and wherein said structure contains at least one $^2H$, $^3H$, $^{32}P$, $^{33}P$ or $^{35}S$ as isotopic label.

2. The phosphoinositide compound of claim 1, wherein said phosphoinositide compound comprises at least a first (poly)unsaturated fattyacyl residue.

3. A synthetic intermediate of an isotopically labelled phosphoinositide compound, said synthetic intermediate comprising temporary protecting groups at hydroxyl and phosphate positions other than the position into which the isotopic label is to be introduced; wherein said synthetic intermediate has one of the myo-inositol-based structures:

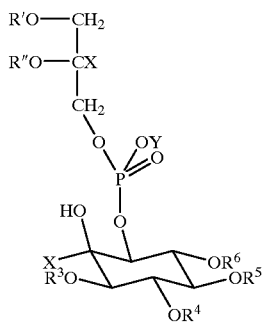

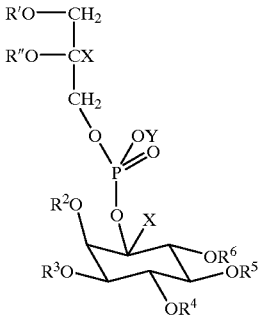

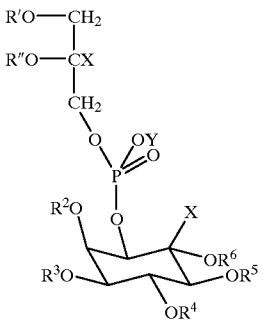

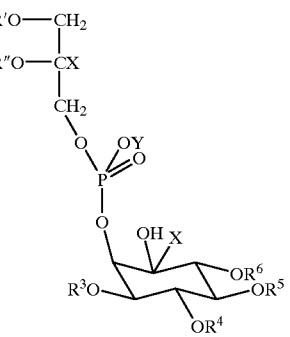

4. A synthetic precursor of a synthetic intermediate in accordance with structures 2, 3, 4, or 5 of claim 3, wherein said synthetic precursor has a ketone group at the position into which an isotopic $^2H$ or $^3H$ label is to be introduced; wherein said synthetic precursor has one of the structures:

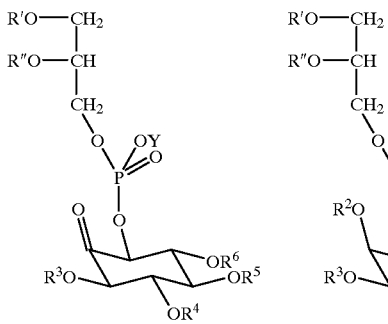

-continued

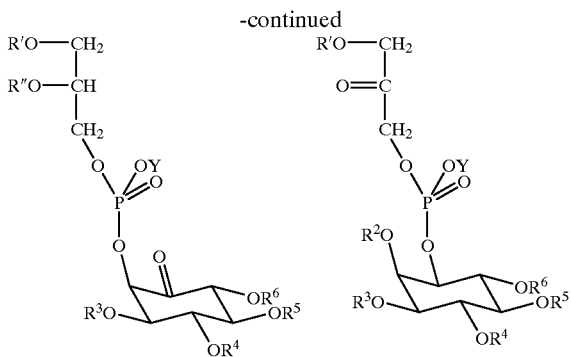

wherein:

Y=alkyl, CH$_3$ or H;

R', R''=fattyacyl, alkyl or H;

R$^3$, R$^4$, R$^5$=(OH protecting group), (Q(T)(O protecting group)$_2$), (Q(T)(OH)(O protecting group) or (Q(T)(OH)$_2$);

R$^2$, R$^6$=H or (OH protecting group); and

Q=P, $^{32}$P or $^{33}$P; T=O or $^{35}$S.

5. A synthetic precursor of a synthetic intermediate in accordance with structure 3 of claim 3, wherein said synthetic precursor has a ketone group at the 1- position into which an isotopic $^2$H or $^3$H label is to be introduced; wherein said synthetic precursor has the structure:

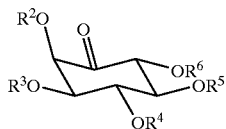

wherein:

R$^3$, R$^4$, R$^5$=(OH protecting group), (Q(T)(O) protecting group)$_2$), (Q)(T)(OH)(O protecting group) or (Q(T)(OH)$_2$);

R$^2$, R$^6$=H or (OH protecting group); and

Q=P, $^{32}$P or $^{33}$P; T=O or $^{35}$S.

wherein:

X=H, $^2$H or $^3$H; Y=alkyl, CH$_3$, H or (O protecting group);

R', R''=fattyacyl, alkyl or H;

R$^3$, R$^4$, R$^5$=(OH protecting group), (Q(T)(O protecting group)$_2$), (Q(T)(OH)(O protecting group) or (Q(T)(OH)$_2$);

R$^2$, R$^6$=H or (OH protecting group);

Q=P, $^{32}$P or $^{33}$P; T=O or $^{35}$S; and wherein said structure contains at least one $^2$H, $^3$H, $^{32}$P, $^{33}$P or $^{35}$S as isotopic label.

6. A synthetic myo-inositol-based precursor of a synthetic intermediate in accordance with structure 3 of claim 3, wherein said synthetic precursor has at least one $^2$H, $^3$H, $^{32}$P, $^{33}$P or $^{35}$S as isotope label and has the structure:

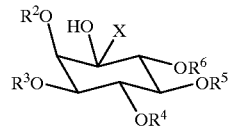

wherein:

X=H, $^2$H or $^3$H;

R$^3$, R$^4$, R$^5$=(OH protecting group), (Q(T)(O protecting group)$_2$), (Q(T)(OH)(O protecting group) or (Q(T)(OH)$_2$);

R$^2$, R$^6$=H or (OH protecting group); and

Q=P, $^{32}$P or $^{33}$P; T=O or $^{35}$S; and wherein said structure contains at least one $^2$H, $^3$H, $^{32}$P, $^{33}$P or $^{35}$S as isotopic label.

7. The phosphoinositide compound of claim 1, wherein said phosphoinositide compound further comprises at least a second stable or radioactive isotope label within the alkyl or fattyacyl residues of said phosphoinositide compound.

8. The phosphoinositide compound of claim 1, wherein said phosphoinositide compound has a structure based on 1D-myo-inositol.

9. The phosphoinositide compound of claim 1, wherein said phosphoinositide compound has a structure based on 1L-myo-inositol.

10. The synthetic intermediate of claim 3, wherein said synthetic intermediate has a structure based on 1D-myo-inositol.

11. The synthetic intermediate of claim 3, wherein said synthetic intermediate has a structure based on 1L-myo-inositol.

12. The synthetic precursor of claim 4, wherein said synthetic precursor has a structure based on 1D-myo-inositol.

13. The synthetic precursor of claim 4, wherein said synthetic precursor has a structure based on 1L-myo-inositol.

14. The synthetic precursor of claim 5, wherein said synthetic precursor has a structure based on 1D-myo-inositol.

15. The synthetic precursor of claim 5, wherein said synthetic precursor has a structure based on 1L-myo-inositol.

16. The synthetic precursor of claim 6, wherein said synthetic precursor has structure based on 1D-myo-inositol.

17. The synthetic precursor of claim 6, wherein said synthetic precursor has structure based on 1L-myo-inositol.

18. The phosphoinositide compound of claim 7, wherein said phosphoinositide compound has a structure based on 1D-myo-inositol.

19. The phosphoinositide compound of claim 7, wherein said phosphoinositide compound has a structure based on 1L-myo-inositol.

20. The phosphoinositide compound of claim 1, wherein said phosphoinositide compound has a structure based on sn-glycero-3-phospho as glycerol residue.

21. The phosphoinositide compound of claim 1, wherein said phosphoinositide compound has a structure based on sn-glycero-1-phospho as glycerol residue.

22. The phosphoinositide compound of claim 1, wherein said phosphoinositide compound has a structure based on rac-glycero-3-phospho as glycerol residue.

23. The synthetic intermediate of claim 3, wherein said synthetic intermediate has a structure based on sn-glycero-3-phospho as glycerol residue.

24. The synthetic intermediate of claim 3, wherein said synthetic intermediate has a structure based on sn-glycero-1-phospho as glycerol residue.

25. The synthetic intermediate of claim 3, wherein said synthetic intermediate has a structure based on rac-glycero-3-phospho as glycerol residue.

26. The synthetic precursor of claim 4 wherein said synthetic precursor has a structure based on sn-glycero-3-phospho as glycerol residue.

27. The synthetic precursor of claim 4, wherein said synthetic precursor has a structure based on sn-glycero-1-phospho as glycerol residue.

28. The synthetic precursor of claim 4, wherein said synthetic precursor has a structure based on rac-glycero-3-phospho as glycerol residue.

29. A substantially purified phosphoinositide compound that comprises at least a first stable or radioactive isotope label within the inositol or glycerol residue of said phosphoinositide compound; wherein said stable or radioactive isotope label is selected from the group consisting of $^2$H, $^3$H, $^{32}$P, $^{33}$P and $^{35}$S and wherein said phosphoinositide compound has the myo-inositol-based structure:

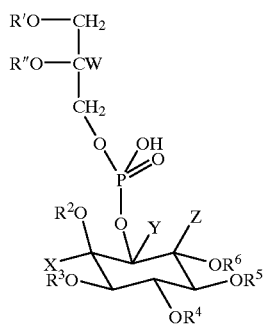

wherein:
R', R"=fattyacyl, alkyl or H;
R$^2$, R$^6$=H or (OH protecting group);
R$^3$, R$^4$, R$^5$=H, (OH protecting group), (Q(T)(O protecting group)$_2$), (Q(T)(OH)(O protecting group) or (Q(T)(OH)$_2$);
Q=P, $^{32}$P or $^{33}$P;
T=O or $^{35}$S;
W, X, Y, Z=$^2$H, $^3$H or H; and
wherein said structure contains temporary protecting groups at hydroxyl and phosphate positions other than the position of at least a first stable or radioactive $^2$H and $^3$H isotope label.

* * * * *

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

Column 27,
Lines 51-62, please delete

"wherein: $X = H, {}^{2}H$ or ${}^{3}H$; $Y$ = alkyl, $CH_3$, H or (O protecting group);
$R'$, $R''$ = fattyacyl, alkyl or H;
$R^3$, $R^4$, $R^5$ = (OH protecting group), $(Q(T)(O \text{ protecting group})_2)$,
$(Q(T)(OH)(O \text{ protecting group})$ or $(Q(T)(OH)_2)$;
$R^2$, $R^6$ = H or (OH protecting group);
$Q = P, {}^{32}P$ or ${}^{33}P$; $T = O$ or ${}^{35}S$; and wherein said structure contains at least one ${}^{2}H$, ${}^{3}H$, ${}^{32}P$, ${}^{33}P$ or ${}^{35}S$ as isotopic label."

Signed and Sealed this

Eighth Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

<u>Columns 25-30,</u>
Claims 1, 3, 6, 8, 9, 10, 11, 12, 13, 14, 15, 16, 17, 18, 19 and 29, at each instance, please delete "myo" and insert -- *myo* -- therefor.

<u>Column 26,</u>
Between structure 3 and 4, please insert -- or --.
after the last structure, please insert the following:
-- wherein: $X = H, {}^{2}H$ or ${}^{3}H$; $Y$ = alkyl, $CH_3$, H or (O protecting group);
$R', R''$ = fattyacyl, alkyl or H;
$R^3, R^4, R^5$ = (OH protecting group), (Q(T)(O protecting group)$_2$),
(Q(T)(OH)(O protecting group) or (Q(T)(OH)$_2$);
$R^2, R^6$ = H or (OH protecting group);
$Q = P, {}^{32}P$ or ${}^{33}P$; $T = O$ or ${}^{35}S$; and
wherein said structure contains at least one ${}^{2}H, {}^{3}H, {}^{32}P, {}^{33}P$ or ${}^{35}S$ as isotopic label. --

<u>Column 27,</u>
Line 43, please delete "(Q(T(O)" and insert -- (Q(T(O -- therefore.

<u>Column 28,</u>
Claims 20, 21, 23 and 24, at each instance, please delete "sn" and insert -- *sn* -- therefor.
Claim 22, at each instance, please delete "rac" and insert -- *rac* -- therefore.

<u>Column 29,</u>
Claims 26 and 27, at each instance, please delete "sn" and insert -- *sn* -- therefor.
Claims 25 and 28, at each instance, please delete "rac" and insert -- *rac* -- therefore.

Signed and Sealed this

Fifteenth Day of October, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

Column 1,
Line 17, delete "10 1." and insert -- 1. --.
Line 18, after "compounds", insert -- comprising --.
Line 26, delete "2'-O-fattyacyl-sn" and insert -- 2'-O-fattyacyl"-sn --.
Line 32, delete "1,'2'-diacyl" and insert -- 1',2'-diacyl --.

Column 3,
Line 32, delete "an" and insert -- a --.

Column 5,
Lines 9-27, in structure to the left delete "$CW_2$," and insert -- CW --.

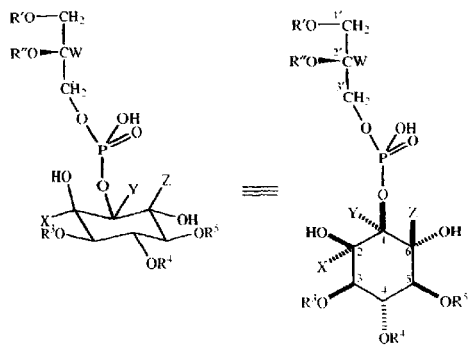

Line 37, delete "basedonthe" and insert -- based on the --.

Column 6,
Line 4, delete "25".
Line 24, delete "1-10glycero" and insert -- 1-glycero --.
Line 44, delete "by" and insert -- be --.

Column 7,
Line 55, after "may", insert -- be --.

Column 9,
Line 62, delete "Bu4NHSO$_4$" and insert -- Bu$_4$NHSO$_4$ --.

UNITED STATES PATENT AND TRADEMARK OFFICE
CERTIFICATE OF CORRECTION

PATENT NO.  : 6,376,697 B1
DATED       : April 23, 2002
INVENTOR(S) : Rajindra Aneja It is certified that error appears in the above-identified patent and that said Letters Patent is hereby corrected as shown below:

Column 12,
Line 24, delete "1-phosphatidyl-1-OH and 1-phosphatidyl-6".
Line 63, delete "1B-1" and insert -- 1D-1 --.

Column 13,
Line 26, delete "di-isopropylphosphoramidite" and insert -- diisopropylphosphoramidite --.

Column 15,
Line 21, delete "steps" and insert -- step --.
Line 44, delete "to obtain".

Column 16,
Line 57, delete "$1_D$" and insert -- 1D --.

Column 20,
Lines 10-48, delete the three structures and insert the following three structures in which the placement of "6" and "49" has been corrected so that these numbers are not superimposed over the structures.

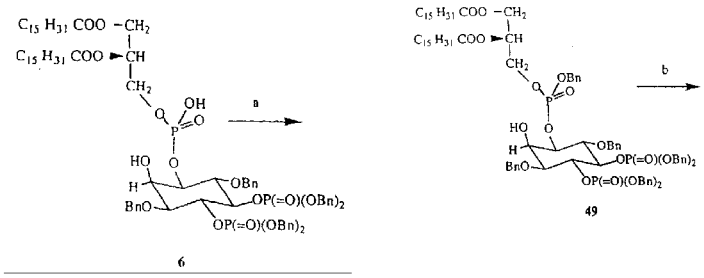

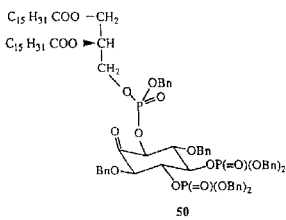

Column 21,
Line 38, delete "protected(phosphates) 'can" and insert -- protected(phosphates) can --.
Line 60, delete "$^1/_3$" and insert -- 1/3 --.

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

Column 22,
Line 14, delete "<" and insert -- > --.
Line 67, delete "3,6-di-myo" and insert -- 3,6-di-O-benzyl-myo --.

Column 23,
Line 3, delete "3,6-di-1-myo" and insert -- 3,6-di-O-benzyl-myo --.
Lines 11 and 12, dlete "the carriage return and By" and insert -- by --.
Line 11, delete "Procedure B:" and insert -- Procedure B. --.
Line 44, delete "1myo" and insert -- 1-myo --.
Line 57, delete "2myo" and insert -- 2-myo --.
Lines 63-64, delete "3,6-1myo" and insert -- 3,6-di-O-benzyl-1-myo --.

Column 24,
Line 10, delete "6" and insert -- 8a --.
Line 14, delete "8a(x=H)" and insert -- 8a(X=H) --
Line 34, center "Example 10 --.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

Column 1,
Line 17, delete "10 1." and insert -- 1. --.
Line 18, after "compounds", insert -- comprising --.
Line 26, delete "2'-O-fattyacyl-sn" and insert -- 2'-O-fattyacyl"-sn --.
Line 32, delete "1,'2'-diacyl" and insert -- 1',2'-diacyl --.

Column 3,
Line 32, delete "an" and insert -- a --.

Column 5,
Lines 9-27, in structure to the left delete "$CW_2$." and insert -- CW --.

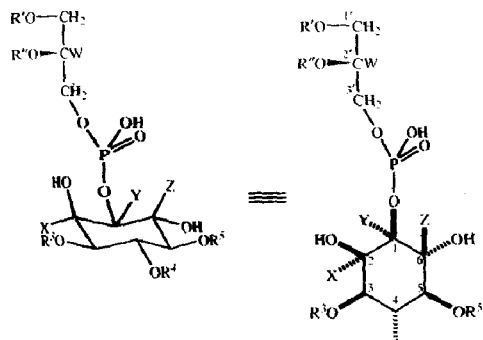

Line 37, delete "basedonthe" and insert -- based on the --.

Column 6,
Line 4, delete "25".
Line 24, delete "1-10glycero" and insert -- 1-glycero --.
Line 44, delete "by" and insert -- be --.

Column 7,
Line 55, after "may", insert -- be --.

Column 9,
Line 62, delete "Bu4NHSO$_4$" and insert -- Bu$_4$NHSO$_4$ --.

UNITED STATES PATENT AND TRADEMARK OFFICE
CERTIFICATE OF CORRECTION

PATENT NO. : 6,376,697 B1  
DATED : April 23, 2002  
INVENTOR(S) : Rajindra Aneja It is certified that error appears in the above-identified patent and that said Letters Patent is hereby corrected as shown below:

Column 12,  
Line 24, delete "1-phosphatidyl-1-OH and 1-phosphatidyl-6".  
Line 63, delete "1B-1" and insert -- 1D-1 --.

Column 13,  
Line 26, delete "di-isopropylphosphoramidite" and insert -- diisopropylphosphoramidite --.

Column 15,  
Line 21, delete "steps" and insert -- step --.  
Line 44, delete "to obtain".

Column 16,  
Line 57, delete "1$_D$" and insert -- 1D --.

Column 20,  
Lines 10-48, delete the three structures and insert the following three structures in which the placement of "6" and "49" has been corrected so that these numbers are not superimposed over the structures.

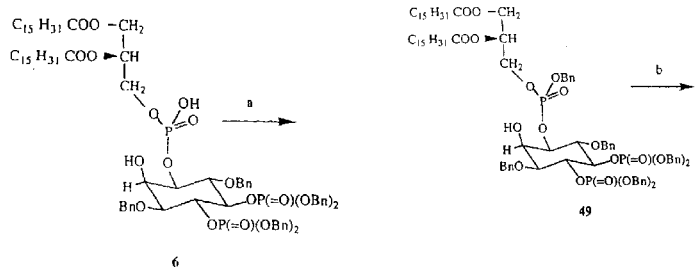

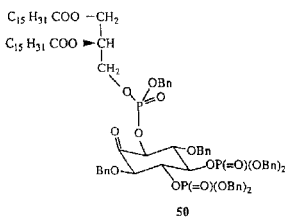

Column 21,  
Line 38, delete "protected(phosphates) 'can" and insert -- protected(phosphates) can --.  
Line 60, delete "$^1/_3$" and insert -- 1/3 --.

UNITED STATES PATENT AND TRADEMARK OFFICE
CERTIFICATE OF CORRECTION

PATENT NO. : 6,376,697 B1
DATED : April 23, 2002
INVENTOR(S) : Rajindra Aneja

It is certified that error appears in the above-identified patent and that said Letters Patent is hereby corrected as shown below:

Column 22,
Line 14, delete "<" and insert -- > --.
Line 67, delete "3,6-di-myo" and insert -- 3,6-di-O-benzyl-myo --.

Column 23,
Line 3, delete "3,6-di-1-myo" and insert -- 3,6-di-O-benzyl-myo --.
Lines 11 and 12, delete "the carriage return and By" and insert -- by --.
Line 11, delete "Procedure B:" and insert -- Procedure B. --.
Line 44, delete "1myo" and insert -- 1-myo --.
Line 57, delete "2myo" and insert -- 2-myo --.
Lines 63-64, delete "3,6-1myo" and insert -- 3,6-di-O-benzyl-1-myo --.

Column 24,
Line 10, delete "6" and insert -- 8a --.
Line 14, delete "8a(x=H)" and insert -- 8a(X=H) --
Line 34, center "Example 10".

Signed and Sealed this

Fourth Day of January, 2005

JON W. DUDAS
*Director of the United States Patent and Trademark Office*